(12) United States Patent
Chen et al.

(10) Patent No.: US 11,773,113 B2
(45) Date of Patent: Oct. 3, 2023

(54) CRYSTAL FORMS OF CRISABOROLE IN FREE FORM AND PREPARATION METHOD AND USE THEREOF

(71) Applicant: Anacor Pharmaceuticals, Inc., New York, NY (US)

(72) Inventors: Minhua Chen, Jiangsu (CN); Yanfeng Zhang, Jiangsu (CN); Fei Lu, Jiangsu (CN); Nan Xia, Jiangsu (CN); Xiaoyu Zhang, Jiangsu (CN)

(73) Assignee: Anacor Pharmaceuticals, Inc., New York, NY (US)

( * ) Notice: Subject to any disclaimer, the term of this patent is extended or adjusted under 35 U.S.C. 154(b) by 1364 days.

(21) Appl. No.: 16/099,839

(22) PCT Filed: May 9, 2017

(86) PCT No.: PCT/CN2017/083631
§ 371 (c)(1),
(2) Date: Nov. 8, 2018

(87) PCT Pub. No.: WO2017/193914
PCT Pub. Date: Nov. 16, 2017

(65) Prior Publication Data
US 2023/0234974 A1   Jul. 27, 2023

(30) Foreign Application Priority Data

May 9, 2016 (CN) .......................... 201610301832.6

(51) Int. Cl.
*C07F 5/02* (2006.01)

(52) U.S. Cl.
CPC .......... *C07F 5/025* (2013.01); *C07B 2200/13* (2013.01)

(58) Field of Classification Search
CPC ...................................................... C07F 5/025
See application file for complete search history.

(56) References Cited

U.S. PATENT DOCUMENTS

| 7,582,621 | B2 * | 9/2009 | Baker ..................... A61P 31/14 |
| | | | 514/64 |
| 8,039,450 | B2 * | 10/2011 | Akama .................. A61P 19/00 |
| | | | 546/290 |
| 8,039,451 | B2 | 10/2011 | Baker et al. |
| 9,353,133 | B2 | 5/2016 | Baker et al. |
| 2007/0286822 | A1 | 12/2007 | Sanders et al. |

FOREIGN PATENT DOCUMENTS

| WO | 2006089067 | 8/2006 |
| WO | 2007078340 | 7/2007 |
| WO | 2007095638 | 8/2007 |
| WO | 2017093857 | 6/2017 |

* cited by examiner

*Primary Examiner* — David K O'Dell
(74) *Attorney, Agent, or Firm* — Feng Shao

(57) ABSTRACT

The present invention relates to four crystal forms of crisaborole in free form and the preparation method thereof. The present invention also relates to the pharmaceutical composition containing the crystal forms and the use thereof.

14 Claims, 16 Drawing Sheets

CRYSTAL FORMS OF CRISABOROLE IN FREE FORM AND PREPARATION METHOD AND USE THEREOF

This application is a 35 U.S.C. 371 National Stage of International Application No. PCT/CN2017/083631 filed May 9, 2017, which claims the benefit of Chinese Application No. CN201610301832.6 filed May 9, 2016, the entire disclosures of each are herein incorporated by reference.

TECHNICAL FIELD

The present invention relates to a pharmaceutical crystal technical field, and particularly, to crystal forms of crisaborole in free form and preparation method and use thereof.

BACKGROUND ART

Polycrystalline form or polycrystalline phenomenon is an inherent attribute of some molecules or molecular compositions. Same molecules may form different crystals due to different arrangements, and these crystals have different crystalline structures and physical properties, for example, such as solubility, stability, thermal property, mechanical property, purification ability, X-ray diffraction pattern, IR absorption pattern, Raman spectrum and solid state NMR. One or more methods for analysis or detection can be used to distinguish different crystal forms of same molecules or molecular compositions.

It is found that novel crystal forms of pharmaceutically active ingredients (including anhydrates, hydrates, and solvates) may produce more workable advantages or provide materials having better physical and chemical characteristics, e.g., better bioavailability, better storage stability, easiness to be processed and treated, and easiness to be purified, or as an intermediate crystal form that can be easily converted into other crystal forms. Some novel crystal forms of pharmaceutically useful compounds also can help medicines to improve their properties. Thus, the novel crystal forms can expand selective forms of raw materials in the pharmaceuticals, e.g., improved dissolution, improved storage time limit, and more easiness to be processed.

Psoriasis and allergic dermatitis are non-infectious inflammatory diseases with a chronic and recurrent course of disease. At present, although some therapies can be used to control these diseases, other therapies are still in study. Appropriate therapies can relieve symptoms and prolong attack intervals. Crisaborole (also called as AN-2728) is a kind of locally-administrated boron-containing compound developed by Anacor Pharmaceuticals Inc., which can inhibit the activity of PDE4, thereby inhibiting the release of TNFalpha, IL-12, IL-23 and other cytokines. Crisaborole has a good therapeutic effect on dermatoses such as psoriasis, allergic dermatitis, etc., and it is approved by the American FDA on Dec. 14, 2016. Crisaborole has the chemical name of 4-[(1,3-dihydro-1-hydroxyl-2,1-benzoxaborolane-5-yl)oxy]benzonitrile, and it is represented by the following chemical formula (I):

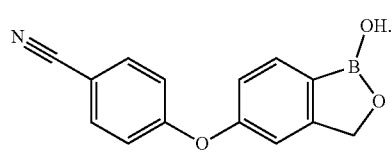

(I)

At present, there is no report regarding crystal forms of crisaborole in the prior art. Thus, it is necessary to comprehensively and systematically screen the polycrystalline forms of crisaborole, so as to select the crystal forms having beneficial properties that can be used for developments of crisaborole products.

The inventors have surprisingly found out four crystal forms of crisaborole during researches. The crystal forms of crisaborole as provided in the invention have good stability, low moisture absorption, homogenous particle size distribution, and a solubility that is in line with medical requirements, and they can be stably stored, thereby avoiding crystal transitions of medicines during developments. Thus, these crystal forms have great values to be developed.

DESCRIPTIONS OF THE INVENTION

Directed to the deficiencies in the prior art, the objective of the invention is to provide crystal forms of crisaborole and the preparation method and use thereof.

According to the objective of the invention, the invention is provided with a crystal form I of crisaborole in free form (hereafter called as "crystal form I").

With Cu-Kα irradiations, the X-ray powder diffraction of the crystal form I has the characteristic peaks at the diffraction angles 2θ: 15.3°±0.2°, 26.1°±0.2°, 14.1°±0.2°.

In a preferred embodiment according to the invention, the X-ray powder diffraction of the crystal form I has the characteristic peaks at the diffraction angles 2θ: 18.1°±0.2°, 24.8°±0.2°, 16.0°±0.2°.

In another preferred embodiment according to the invention, the X-ray powder diffraction of the crystal form I has the characteristic peaks at the diffraction angles 2θ: 28.4°±0.2°, 21.4°±0.2°, 6.0°±0.2°.

In a further preferred embodiment according to the invention, the X-ray powder diffraction of the crystal form I has the characteristic peaks at the diffraction angles 2θ: 15.3°±0.2°, 26.1°±0.2°, 14.1°±0.2°, 18.1°±0.2°, 24.8°±0.2°, 16.0°±0.2, 28.4°±0.2°, 21.4°±0.2°, 6.0°±0.2°.

Non-limitedly, in a specific embodiment according to the invention, the X-ray powder diffraction pattern of the crystal form I is shown in FIG. 1.

According to the objective of the invention, the invention is further provided with a method of preparing the crystal form I, comprising the following steps:

1) solids of crisaborole in free form are dissolved in a single volatile solvent until the resultant mixture is clear, and the resultant mixture performs volatile crystallization, to produce solids of crystal form I, wherein the single volatile solvent is selected from alkyl nitriles, alkyl ethers, halogenated hydrocarbons and esters, wherein:

the alkyl nitrile solvent is acetonitrile, the alkyl ether solvent is methyl(t-butyl) ether, the halogenated hydrocarbon solvent is chlorinated hydrocarbon, and preferably, the chlorinated hydrocarbon is selected from chloroform and dichloromethane, and the ester solvent is ethyl acetate; and wherein the volatile crystallization is conducted at room temperature, or 2) solids of crisaborole in free form are suspended in a single solvent or a mixed solvent to produce a suspension, and the suspension is stirred, subjected to centrifugal separation, and dried, to produce the solids of crystal form I, wherein: the single solvent comprises, but not limited to, water and aromatic hydrocarbons, preferably water and toluene, the mixed solvent is a mixed solvent of water with a further solvent selected from the group of alcohols, alkyl nitriles, esters, ketones, amides, cyclic ethers or dimethyl sulfoxide, wherein the volume ratio of water to the further solvent is in the range between 4:3 and 5:1; or the mixed solvent is a mixed solvent of saturated fatty hydrocarbons with ketones, esters, cyclic ethers, halogenated hydrocarbons or alcohols, wherein the volume ratio of the saturated fatty hydrocarbons to the ketones, the esters, the cyclic ethers, the halogenated hydrocarbons or the alcohols is preferably in the range from 5:4 to 7:1; or the mixed solvent is a mixed solvent of aromatic hydrocarbons with halogenated hydrocarbons, wherein the volume ratio of the aromatic hydrocarbons to the halogenated hydrocarbons is preferably 5:4.

Preferably, the mixed solvent is a mixed solvent of water with methanol, acetonitrile, isopropyl acetate, 1,4-dioxane, acetone, dimethyl formamide or dimethyl sulfoxide.

Preferably, the mixed solvent is a mixed solvent of n-heptane with methyl isobutyl ketone, ethyl acetate, 2-methyltetrahydrofuran, chloroform or ethanol.

Preferably, the mixed solvent is a mixed solvent of toluene and dichloromethane.

The temperature is preferably from room temperature to 50° C.

According to the objective of the invention, the invention is provided with crystal form II of Crisaborole in free form (hereafter called as "crystal form II").

With Cu-Kα irradiations, the X-ray powder diffraction of the crystal form II has the characteristic peaks at the diffraction angles 2θ: 20.8°±0.2°, 16.6°±0.2°, 22.6°±0.2°.

In a preferred embodiment according to the invention, the X-ray powder diffraction of the crystal form II has the characteristic peaks at the diffraction angles 2θ: 27.9°±0.2°, 21.8°±0.2°, 17.6°±0.2°.

In another preferred embodiment according to the invention, the X-ray powder diffraction of the crystal form II has the characteristic peaks at the diffraction angles 2θ: 18.4°±0.2°, 21.4°±0.2°, 23.1°±0.2°.

In a further preferred embodiment according to the invention, the X-ray powder diffraction of the crystal form II has the characteristic peaks at the diffraction angles 2θ: 20.8°±0.2°, 16.6°±0.2°, 22.6°±0.2°, 27.9°±0.2°, 21.8°±0.2°, 17.6°±0.2°, 18.4°±0.2°, 21.4°±0.2°, 23.1°±0.2°.

Non-limitedly, in a specific embodiment according to the invention, the X-ray powder diffraction pattern of the crystal form II is shown in FIG. 4.

According to the objective of the invention; the invention is further provided with a method of preparing the crystal form II, comprising the following steps:

1) solids of crisaborole in free form are suspended in a mixed solvent of water and an alcohol to produce a suspension, and the suspension is stirred, subjected to centrifugal separation and dried, to provide the solids of the crystal form II, wherein the water to alcohol volume ratio is 1:1, wherein
    the alcohol is preferably methanol, and
    the stirring and separating steps each are conducted at room temperature; or 2) solids of crisaborole in free form are dissolved in a positive solvent, and then a reverse solvent is added thereto; the resultant mixture crystallized while being stirred, separated and dried, to produce the solids of crystal form II, wherein the solids of crisaborole in free form are present in the positive solvent in a state that the solids are dissolved until the resultant mixture is clear or in a state that the solids are completely dissolved, and the reverse solvent is added until solids are produced;

the positive solvent includes, but not limited to, alcohols, ketones, cyclic ethers, amides, and dimethyl sulfoxide, and the inverse solvent is preferably water, wherein:
    the alcohol solvent is isopropanol,
    the ketone solvent is acetone,
    the cyclic ether solvent is selected from tetrahydrofuran, and 1,4-dioxane, and
    the amide solvent is dimethylformamide; and
    the stirring crystallizing step and the separating step both are conducted at room temperature.

According to the objective of the invention, the invention is provided with crystal form III of crisaborole in free form (hereafter called as "crystal form III").

With Cu-Kα irradiations, the X-ray powder diffraction of the crystal form III has the characteristic peaks at the diffraction angles 2θ: 20.6°±0.2°, 27.8°±0.2°, 18.6°±0.2°.

In a preferred embodiment according to the invention, the X-ray powder diffraction of the crystal form III has the characteristic peaks at the diffraction angles 2θ: 13.6°±0.2°, 19.5°±0.2°, 21.7°±0.2°.

In another preferred embodiment according to the invention, the X-ray powder diffraction of the crystal form III has the characteristic peaks at the diffraction angles 2θ: 21.3°±0.2°, 16.3°±0.2°, 22.5°±0.2°.

In a further preferred embodiment according to the invention, the X-ray powder diffraction of the crystal form III has the characteristic peaks at the diffraction angles 2θ: 20.6°±0.2°, 27.8°±0.2°, 18.6°±0.2°, 13.6±0.2°, 19.5°±0.2°, 21.7°±0.2°, 21.3°±0.2°, 16.3°±0.2°, 22.5°±0.2°.

Non-limitedly, in a specific embodiment according to the invention, the X-ray powder diffraction pattern of the crystal form III is shown in FIG. 7.

According to the objective of the invention, the invention is further provided with a method of preparing the crystal form III, comprising the following steps: solids of crisaborole in free form are dissolved in a ketone solvent until the resultant mixture is clear, and the resultant mixture is subjected to volatile crystallization, to produce the solids of crystal form III, wherein
    the ketone solvent is preferably acetone, and
    the volatile crystallization is conducted at room temperature.

According to the objective of the invention, the invention is provided with crystal form IV of Crisaborole in free form (hereafter called as "crystal form IV").

With Cu-Kα irradiations, the X-ray powder diffraction of the crystal form IV has the characteristic peaks at the diffraction angles 2θ: 20.0°±0.2°, 18.6°±0.2°, 26.4°±0.2°.

In a preferred embodiment according to the invention, the X-ray powder diffraction of the crystal form IV has the characteristic peaks at the diffraction angles 2θ: 5.3°±0.2°, 24.9°±0.2°, 23.2°±0.2°.

In another preferred embodiment according to the invention, the X-ray powder diffraction of the crystal form IV has the characteristic peaks at the diffraction angles 2θ: 17.2°±0.2°, 21.4°±0.2°, 13.0°±0.2°.

In a further preferred embodiment according to the invention, the X-ray powder diffraction of the crystal form IV has the characteristic peaks at the diffraction angles 2θ: 20.0°±0.2°, 18.6°±0.2°, 26.4°±0.2°, 5.3°±0.2°, 24.9°±0.2°, 23.2°±0.2°, 17.2°±0.2°, 21.4°±0.2°, 13.0°±0.2°.

Non-limitedly, in a specific embodiment according to the invention, the X-ray powder diffraction pattern of the crystal form IV is shown in FIG. 10.

According to the objective of the invention, the invention is further provided with a method of preparing the crystal form IV, the method comprising the following steps: solids of crisaborole in free form, the crystal form I, the crystal form II or the crystal form III are heated to a temperature from 120° C. to 150° C., to produce the solids of crystal form IV. Preferably, the temperature is at 130° C. to 145° C.

According to the objective of the invention, the invention is further provided with a pharmaceutical composition, comprising a therapeutically effective dose and/or a prophylactically effective dose of the crystal form I of crisaborole in free form, or the crystal form II of crisaborole in free form, or the crystal form III of crisaborole in free form, or the crystal form IV of crisaborole in free form, as above described, or a combination of these crystal forms, and at least one pharmaceutically acceptable carrier or vehicle.

The invention relates to use of the crystal form I of crisaborole in free form, or the crystal form II of crisaborole in free form, or the crystal form III of crisaborole in free form, or the crystal form IV of crisaborole in free form, or a combination of these crystal forms in the production of medicine formulations for treating psoriasis and allergic dermatitis.

The term "room temperature" in the invention refers to the temperature from 15 to 25° C.

In the invention, the "2θ" expresses the same meaning as that of the "2theta".

The "stirring" is accomplished by using conventional methods in the art, e.g., magnetic stirring or mechanical stirring, with the stirring speed of 50 to 1800 r/m, preferably from 300 to 900 r/m, and most preferably 500 r/m.

The "separation" is accomplished by using conventional methods in the art, e.g., centrifugation or filtration. The "centrifugation" comprises the following operations: a sample to be separated is placed in a centrifugal tube and centrifuged in a speed of 10000 r/m until all solids therein are deposited at the bottom of the centrifugal tube.

Unless specifically described, the "drying" may be carried out at room temperature or a higher temperature. The drying temperature is in the range of from room temperature to about 60° C., or from room temperature to 40° C.; or from room temperature to 50° C. The drying time is in the range from 2 to 48 hours or the drying continues overnight. The drying is carried out in a fume hood, a forced air oven or a vacuum oven.

In the invention, the "crystals" or "crystal forms" refer to those as confirmed by X-ray diffraction pattern. Thus, a person skilled in the art could understand that the physical and chemical properties as discussed here may be characterized, wherein experimental errors depend on conditions of apparatus, sample preparations and sample purity. In particular, a person skilled in the art could well know that the X-ray diffraction pattern usually will vary with changes in conditions of associated apparatus. It should be particularly pointed out that the relative intensity of the X-ray diffraction pattern also varies with the changes in experimental conditions. Thus, the order of peak intensities cannot be used as a unique or crucial factor. In addition; the diffraction angle 2θ usually allows the error at ±0.2°. Moreover, due to effects of experimental factors, such as sample height, peak angles will be deviated in a whole, and usually, certain deviations are allowable. Hence, a person skilled in the art can understand that the X-ray diffraction pattern of a crystal form in the invention does not have to be in line with the X-ray diffraction pattern in the examples as indicated here. Any crystal forms having the same or similar peaks to the peaks in these patterns fall into the scope of the invention. A person skilled in the art could compare the patterns as listed in the invention with a pattern of any unknown crystal form, to prove whether the two patterns reveal the same or different crystal forms.

The terms "crystal forms" and "polycrystalline forms" and other related terms refer to the presence of solid compounds in a crystal structure with a specific crystal form in the invention. Differences in physical and chemical properties of the polycrystalline forms may be reflected in the aspects of storage stability; compressibility, density; and dissolution rate. In an extreme case, differences in solubility and dissolution rate will result in drug inefficiency; even toxicity.

It should be illustrated that the values or numerical ranges as mentioned in the invention should not be narrowly understood as the values or numerical ranges per se, and a person skilled in the art should understand them according to different specific technical circumstances. On the basis of no deviations of the spirits and rules of the invention, the specific values may vary. In the invention, such floating ranges that are predictable for a person skilled in the art are usually expressed by the wording "about".

BRIEF DESCRIPTIONS OF THE DRAWINGS

DESCRIPTION OF EMBODIMENTS OF THE INVENTION

Figure 1:
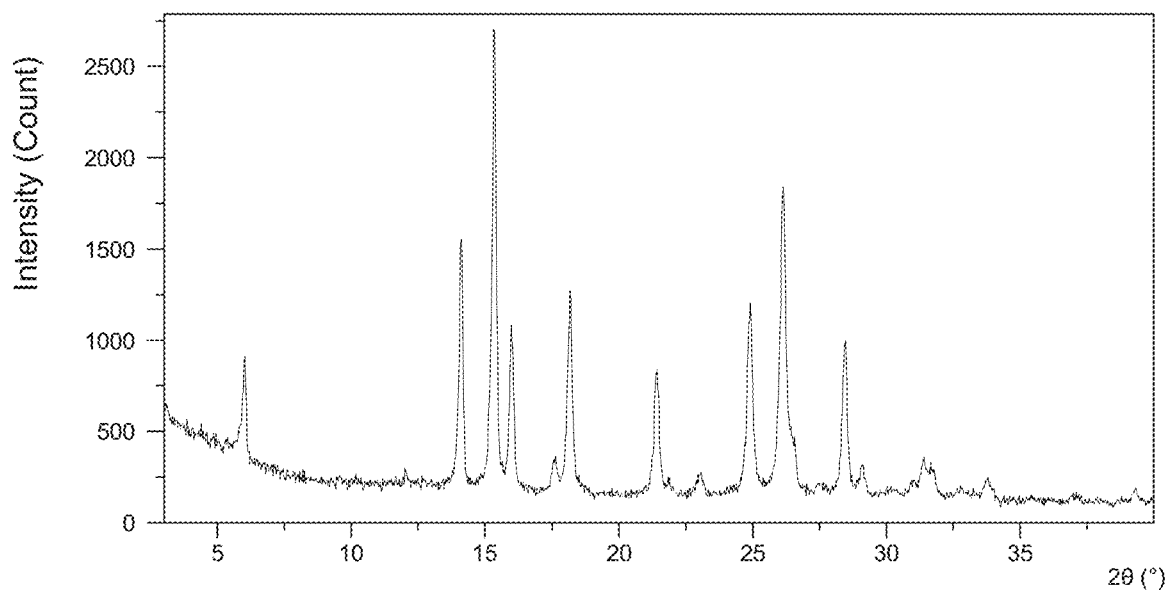
FIG. 1 is the X-ray powder diffraction pattern of the crystal form I as prepared in Example 1 of the invention.

The invention is defined by further referring to the following examples. The examples describe in detail a method of preparing the crystal forms according to the invention and a method of using the same. It is obvious for a person skilled in the art that variations to the material and methods can be made in the case of no deviation from the scope of the invention.

Apparatus and Methods as Used for Collecting Data:

The abbreviations as used in the invention are explained as follows:

XRPD: X-ray powder diffraction,
DSC: Differential scanning calorimetric analysis,
TGA: Thermogravimetric analysis,
DVS: Dynamic vapor sorption,
PSD: Particle size distribution,
PLM: Polarizing microscope
HPLC: High performance Liquid Chromatography The X-ray powder diffraction pattern as described in the invention was collected on a Panalytical Empyrean X-ray powder diffraction meter. The X-ray powder diffraction method has the following parameters:

X-ray reflection parameters: Cu, Kα,
Kα1(Å): 1.540598; Kα2(Å): 1.544426,
Kα2/Kα1 intensity ratio: 0.50,
Voltage: 45 kilovolt (kV),
Current: 40 milliampere (mA),
Scanning scope: from 3.0° to 40.0°.

The differential scanning calorimetric (DSC) pattern as described in the invention was collected on a TA Q2000. The differential scanning calorimetric (DSC) method has the following parameters:

Scanning speed: 10° C./min,
Protective gas: nitrogen gas.

The thermogravimetric analysis (TGA) pattern as described in the invention was collected on a TA Q500. The thermogravimetric analysis (TGA) method has the following parameters:

Scanning speed: 10° C./min,
Protective gas: nitrogen gas.

The dynamic vapor sorption (DVS) pattern as described in the invention was collected on an intrinsic dynamic vapor sorption meter as produced by Surface Measurement Systems Ltd. The dynamic vapor sorption method has the following parameters:

Temperature: 25° C.,
Loading gas, flowing speed: N2, 200 ml/min,
Variation in mass per time: 0.002%/minute,
Relative humidity range: 0% RH-95% RH.

The particle size distribution (PSD) results as described in the invention were collected on a S3500-type laser particle size analytic meter as produced by Microtrac Company. The Microtrac S3500 is equipped with a SDC (Sample Delivery Controller) feeding system. The test was conducted via a wet process, and the dispersion medium as used in the test was Isopar G. The laser particle size analytic meter has the following parameters:

| | |
|---|---|
| Particle size distribution: volume distribution | Collection time: 10 seconds |
| Dispersion medium: Isopar G | Particle size coordination: standard |
| Collection frequency: 3 times | Refractive index of dispersion medium: 1.42 |
| Transparency: transparent | Residual: on |
| Particle refractive index: 1.5 | Flowing rate: 60* |
| Particle shape: irregular | Filtration: on |

*the flowing rate 60% is meant to 60% of the flowing rate 65 ml/second.

The high performance liquid chromatography (HPLC) data were collected in an Agilent 1260, and the used detector was a diode array detector (DAD). The HPLC method as described in the invention has the following parameters:

1. Chromatographic column: Waters Xbridge C18 150× 4.6 mm, 5 μm

2. Flowing phase: A: 0.1% trifluoro acetic acid aqueous solution

B: 0.1% trifluoro acetic acid solution in acetonitrile

The eluting gradient is shown in the following table:

| Time (minute) | % flowing phase B |
|---|---|
| 0.0 | 10 |
| 3.0 | 10 |
| 20.0 | 90 |
| 25.0 | 90 |
| 25.1 | 10 |
| 30.0 | 10 |

3. flowing rate: 1.0 mL/min
4. Injection volume: 5 μL
5. Detection wavelength: 254 nm
6. Column temperature: 40° C.
7. Diluent: 50% acetonitrile.

In the following examples, unless specifically stated, the term "room temperature" refers to the temperature range from 15 to 25° C.

The solids of crisaborole in free form used in the following examples can be commercially available.

Example 1

202.5 mg of solids of crisaborole in free form were added to 6 mL of a mixed solvent system (methanol:water, with the volume ratio 1:5), and the resultant mixture was stirred at 50° C. for 5 days. The reaction mixture was subjected to centrifugal separation and vacuum dried at room temperature, to produce white solid crystals.

It was found that the resultant solid crystals were the crystal form I as described in the invention by detection. The X-ray powder diffraction pattern of the crystal form is shown in FIG. 1, and the corresponding X-ray powder diffraction data are shown in Table 1.

Figure 2:
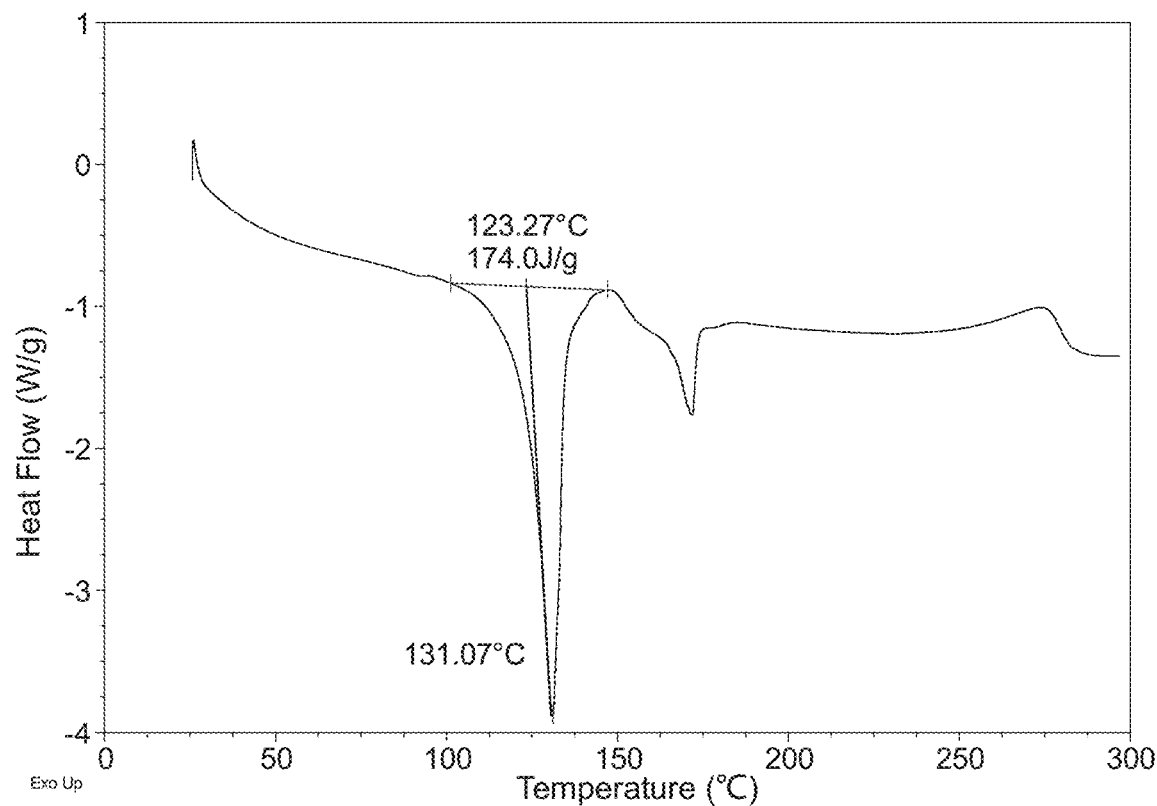
FIG. 2 is the DSC pattern of the crystal form I as prepared in Example 1 of the invention.
Figure 3:
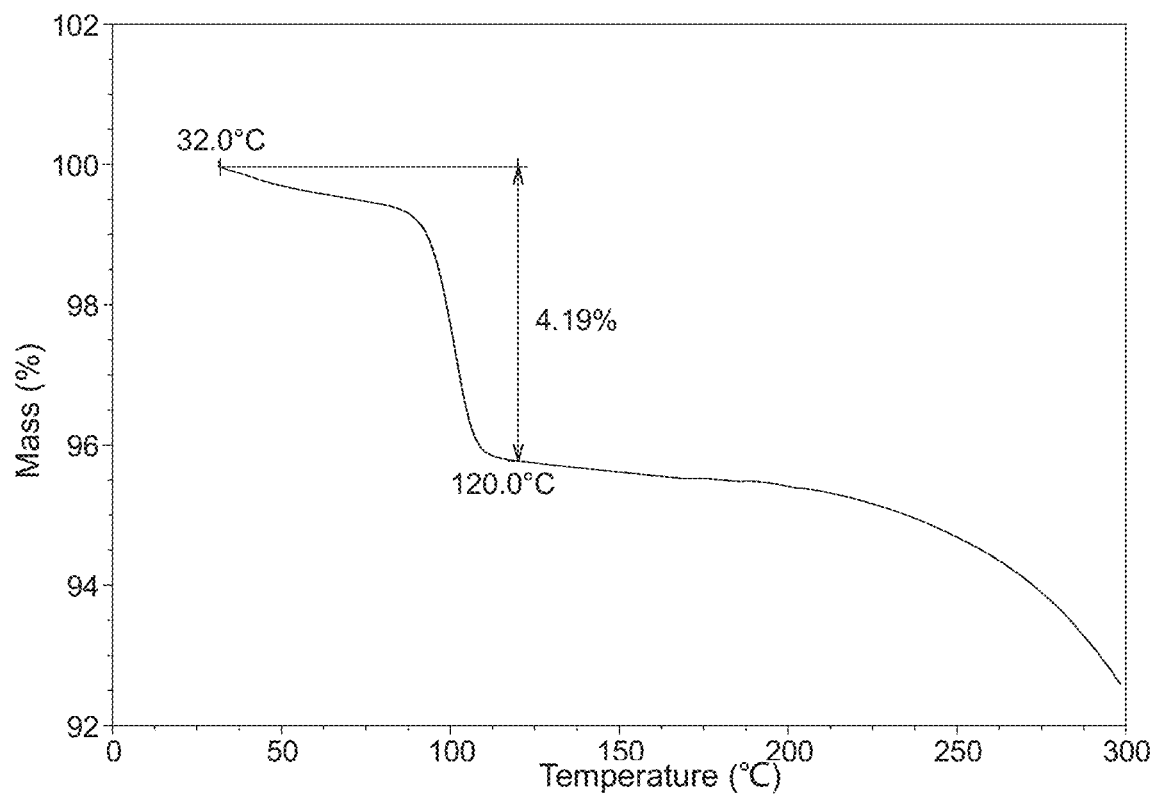
FIG. 3 is the TGA pattern of the crystal form I as prepared in Example 1 of the invention.

Upon conducting the differential scanning calorimetric analysis, the crystal form I, when being heated to a temperature in the vicinity of 123° C., involved heat absorption peaks, and its DSC is shown in FIG. 2. Upon conducting the thermogravimetric analysis, the crystal form I, when being heated to 120° C., had a mass lose gradient of about 4.2%, and its TGA is shown in FIG. 3. The crystal form I according to the invention is a hydrate.

TABLE 1

| 2theta | d-spacing | Intensity % |
| --- | --- | --- |
| 5.98 | 14.79 | 21.09 |
| 11.98 | 7.39 | 2.61 |
| 14.07 | 6.29 | 53.95 |
| 15.31 | 5.79 | 100.00 |
| 15.96 | 5.55 | 33.66 |
| 17.56 | 5.05 | 6.53 |
| 18.14 | 4.89 | 42.95 |
| 21.34 | 4.16 | 26.11 |
| 24.86 | 3.58 | 39.83 |
| 26.09 | 3.42 | 65.72 |
| 28.40 | 3.14 | 31.42 |
| 31.33 | 2.85 | 7.91 |
| 31.68 | 2.82 | 5.53 |
| 39.24 | 2.30 | 2.84 |

Example 2

51.4 mg of solids of crisaborole in free form were added to 1 mL of acetonitrile solvent. After the solids were dissolved in the solvent, the solvent volatilized at room temperature when exposed to air until it completely volatilized, to produce white solid crystals.

Figure 13:
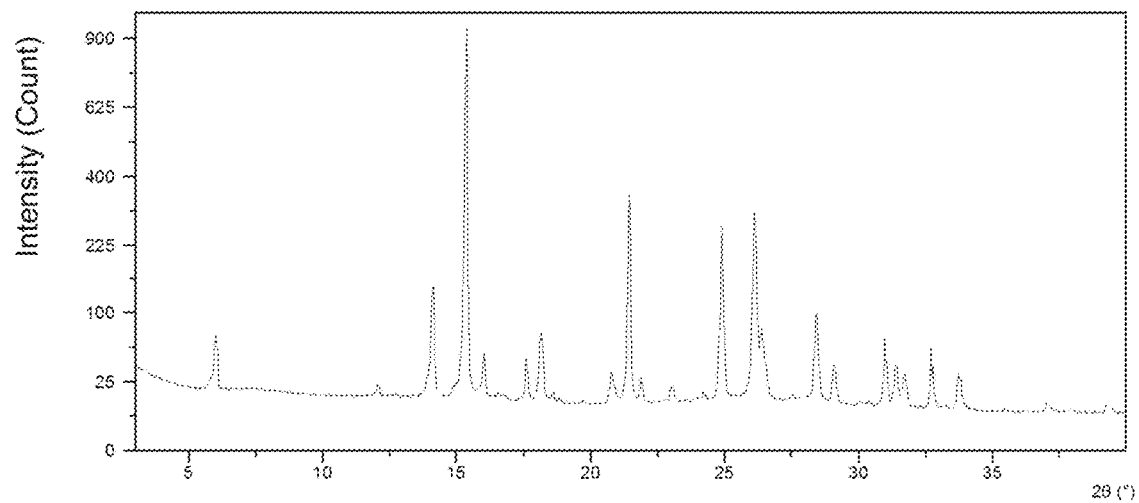
FIG. 13 is the X-ray powder diffraction pattern of the crystal form I as prepared in Example 2 of the invention.

It was found that the resultant solid crystals were the crystal form I as described in the invention by detection, and the X-ray powder diffraction data are shown in FIG. 13 and Table 2.

TABLE 2

| 2theta | d-spacing | Intensity % |
| --- | --- | --- |
| 5.99 | 14.76 | 5.42 |
| 12.02 | 7.36 | 1.01 |
| 14.06 | 6.30 | 14.60 |
| 15.33 | 5.78 | 100.00 |
| 15.99 | 5.54 | 4.06 |
| 17.56 | 5.05 | 3.30 |
| 18.12 | 4.90 | 6.76 |
| 20.73 | 4.28 | 2.27 |
| 21.40 | 4.15 | 38.10 |
| 21.85 | 4.07 | 1.80 |
| 23.00 | 3.87 | 1.32 |
| 24.85 | 3.58 | 24.19 |
| 26.09 | 3.41 | 33.54 |
| 26.35 | 3.38 | 7.30 |
| 28.39 | 3.14 | 9.99 |
| 29.05 | 3.07 | 3.25 |
| 30.94 | 2.89 | 6.24 |
| 31.35 | 2.85 | 3.33 |
| 31.68 | 2.82 | 2.59 |

TABLE 2-continued

| 2theta | d-spacing | Intensity % |
| --- | --- | --- |
| 32.66 | 2.74 | 4.91 |
| 33.69 | 2.66 | 2.40 |

The data in Table 3 were obtained by using the same method as described in Example 2. A certain mass quantity of solids of crisaborole in free form were added to a certain volume of solvent. After the solids were dissolved in the solvent, the solvent volatilized at room temperature when exposed to air until the solvent completely volatilized, to produce white solid crystals. The solids were checked by XRPD to be the crystal form I.

TABLE 3

| No. | Mass of raw material (mg) | Solvent | Solvent volume (mL) | Resultant crystal form |
| --- | --- | --- | --- | --- |
| 1 | 13.1 | Ethyl acetate | 1.0 | Crystal form I |
| 2 | 13.0 | Methyl(t-butyl)ether | 1.0 | Crystal form I |
| 3 | 13.5 | Chloroform | 1.0 | Crystal form I |
| 4 | 13.4 | dichloromethane | 1.0 | Crystal form I |

Example 3

30.7 mg of solids of crisaborole in free form were added to 1.5 mL of water solvent, and the resultant mixture was magnetically stirred at room temperature for two days. The reaction mixture was subjected to centrifugal separation and vacuum dried at room temperature, to produce white solid crystals.

Figure 14:
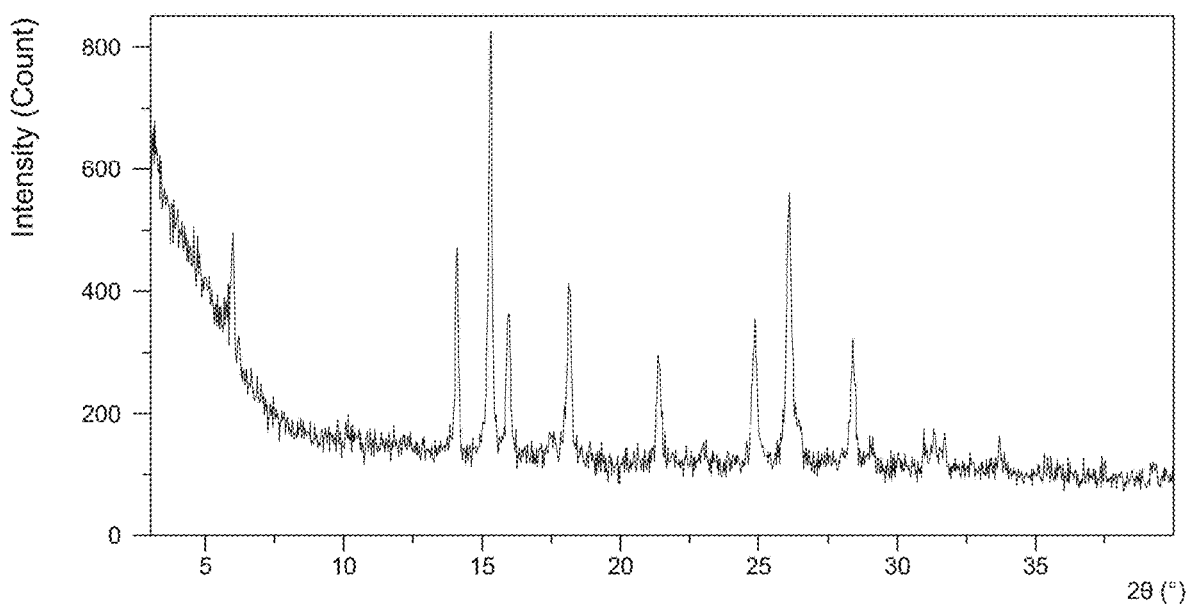
FIG. 14 is the X-ray powder diffraction pattern of the crystal form I as prepared in Example 3 of the invention.

It was found that the resultant solid crystals were the crystal form I as described in the invention by detection, and the X-ray powder diffraction data of the crystal form are shown in FIG. 14 and Table 4.

TABLE 4

| 2theta | d-spacing | Intensity % |
| --- | --- | --- |
| 5.95 | 14.86 | 27.13 |
| 14.03 | 6.31 | 48.74 |
| 15.28 | 5.80 | 100.00 |
| 15.93 | 5.56 | 34.94 |
| 18.12 | 4.90 | 41.14 |
| 21.33 | 4.16 | 24.57 |
| 24.83 | 3.59 | 34.19 |
| 26.06 | 3.42 | 62.24 |
| 28.34 | 3.15 | 27.26 |
| 31.32 | 2.86 | 5.69 |
| 33.63 | 2.67 | 4.16 |

The data in Table 5 were obtained by using the same method as described in Example 3. A certain mass quantity of solids of crisaborole in free form were added to a certain volume of solvent, and the resultant mixture was magnetically stirred at room temperature. The reaction mixture was subjected to centrifugal separation and vacuum dried at room temperature, to produce white solid crystals. The resultant solids were determined by the XRPD to be the crystal form I.

TABLE 5

| No. | Mass of starting material (mg) | Solvent | Solvent volume (mL) | Resultant crystal form |
|---|---|---|---|---|
| 1 | 30.2 | toluene | 1.0 | Crystal form I |
| 2 | 31.6 | Acetonitrile/water | 0.6/0.8 | Crystal form I |
| 3 | 30.8 | Isopropyl acetate/water | 0.2/0.8 | Crystal form I |
| 4 | 29.6 | 1,4-dioxane/water | 0.4/0.8 | Crystal form I |
| 5 | 30.5 | Acetone/water | 0.4/0.8 | Crystal form I |
| 6 | 29.9 | Dimethyl formamide/water | 0.6/0.8 | Crystal form I |
| 7 | 29.8 | Dimethyl sulfoxide/water | 0.6/0.8 | Crystal form I |
| 8 | 29.1 | methylisobutylketone/n-heptane | 0.6/0.5 | Crystal form I |
| 9 | 30.3 | Ethyl acetate/n-heptane | 0.6/0.5 | Crystal form I |
| 10 | 29.0 | 2-methyltetrahydrofuran/n-heptane | 0.4/0.5 | Crystal form I |
| 11 | 30.3 | Chloroform/n-heptane | 0.4/0.5 | Crystal form I |
| 12 | 31.4 | ethanol/n-heptane | 0.2/1.3 | Crystal form I |
| 13 | 30.2 | dichloromethane/toluene | 0.4/0.5 | Crystal form I |
| 14 | 29.7 | isopropanol/water | 0.6/0.8 | Crystal form I |

Example 4

34.5 mg of solids of crisaborole in free form were added to 1.6 mL of a mixed solvent system (methanol:water, with the volume ratio 1:1). The resultant mixture was magnetically stirred at room temperature, and then it was subjected to centrifugal separation and vacuum dried at room temperature, to produce white solid crystals.

Figure 4:
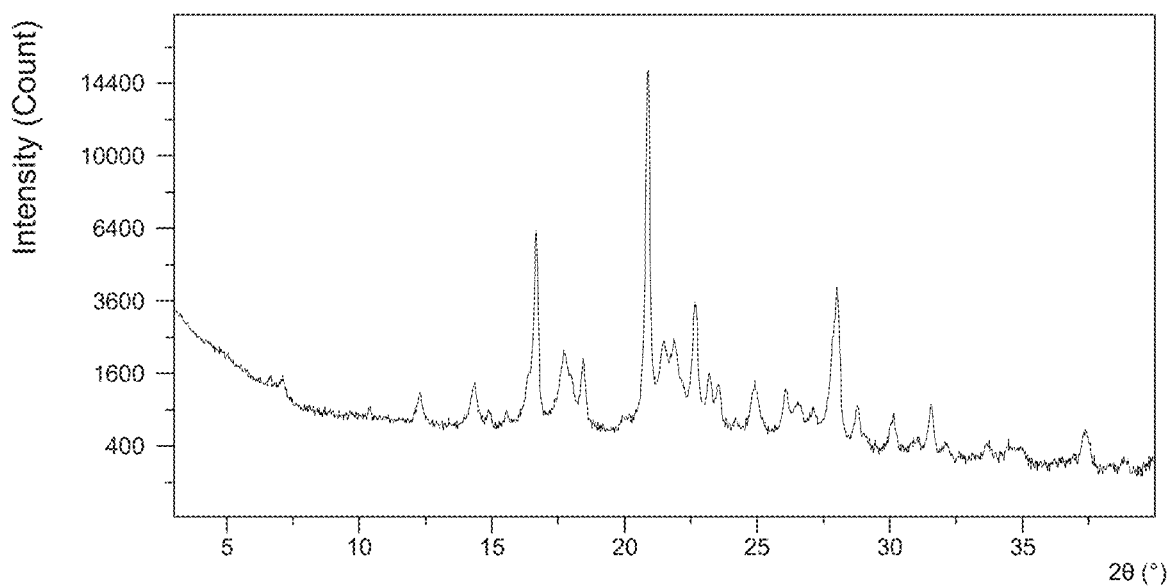
FIG. 4 is the X-ray powder diffraction pattern of the crystal form II as prepared in Example 4 of the invention.

It was found that the resultant solid crystals were the crystal form II as described in the invention by detection. The X-ray powder diffraction pattern of the crystal form is shown in FIG. 4, and the corresponding X-ray powder diffraction data are shown in Table 6.

Figure 5:
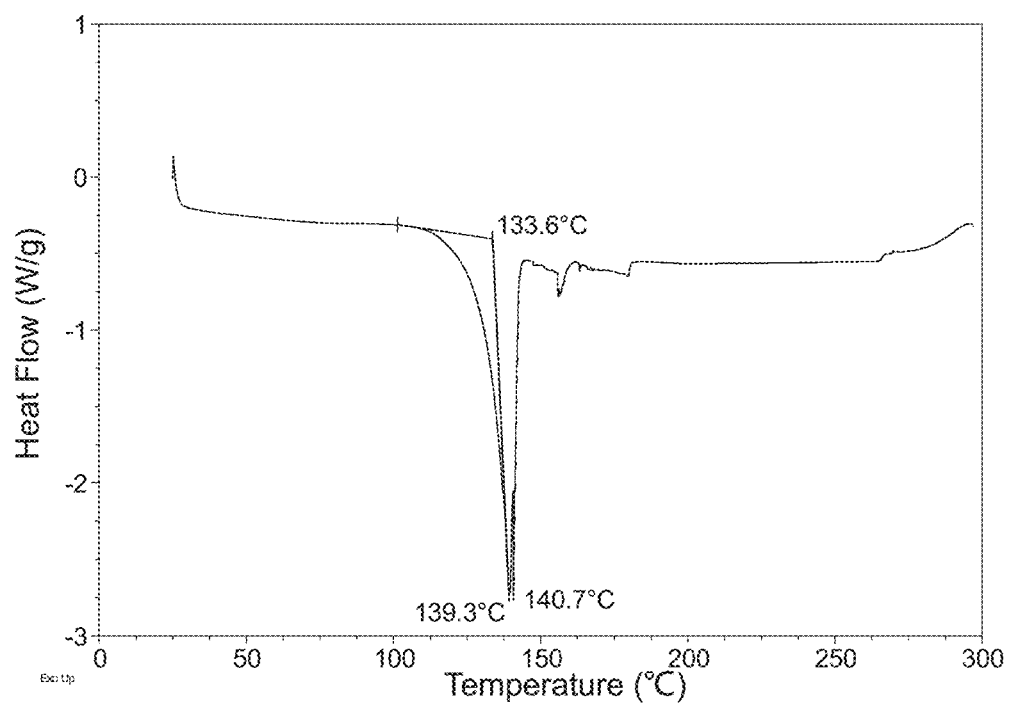
FIG. 5 is the DSC pattern of the crystal form II as prepared in Example 4 of the invention.
Figure 6:
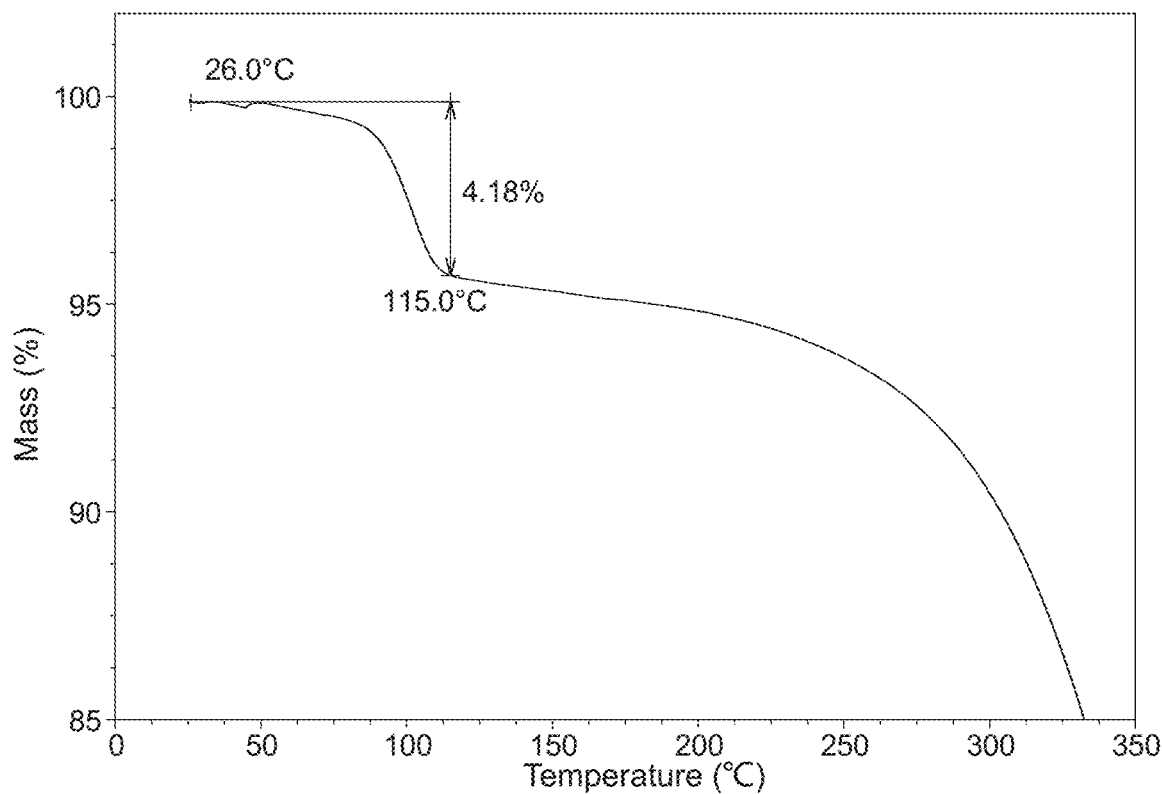
FIG. 6 is the TGA pattern of the crystal form II as prepared in Example 4 of the invention.

Upon conducting the differential scanning calorimetric analysis, the crystal form II, when being heated to a temperature in the vicinity of 134° C., involved heat absorption peaks, and its DSC is shown in FIG. 5. Upon conducting the thermogravimetric analysis, the crystal form II, when being heated to 115° C., had a mass lose gradient of about 4.2%, and its TGA is shown in FIG. 6. The crystal form II according to the invention is a hydrate.

TABLE 6

| 2theta | d-spacing | Intensity % |
|---|---|---|
| 7.01 | 12.61 | 2.38 |
| 12.17 | 7.27 | 3.50 |
| 14.21 | 6.23 | 4.68 |
| 14.77 | 6.00 | 1.50 |
| 16.55 | 5.36 | 37.69 |
| 17.60 | 5.04 | 9.92 |
| 18.32 | 4.84 | 8.97 |
| 20.76 | 4.28 | 100.00 |
| 21.35 | 4.16 | 11.45 |
| 21.75 | 4.09 | 11.77 |
| 22.55 | 3.94 | 19.21 |
| 23.08 | 3.85 | 6.09 |
| 23.43 | 3.80 | 4.61 |
| 25.97 | 3.43 | 4.66 |
| 27.00 | 3.30 | 2.75 |
| 27.89 | 3.20 | 24.06 |
| 28.65 | 3.12 | 3.74 |
| 30.03 | 2.98 | 3.15 |
| 31.44 | 2.85 | 4.29 |
| 37.29 | 2.41 | 2.50 |

Example 5

30.3 mg of solids of crisaborole in free form were added to 0.4 mL of isopropanol solvent, and 0.6 mL of the reverse solvent water were dropwise added thereto while being magnetically stirred at room temperature. The resultant mixture crystallized while being stirred for 5 days, and then it was subjected to centrifugal separation and vacuum dried at room temperature, to produce white solid crystals.

It was found that the resultant solid crystals were the crystal form II as described in the invention by detection, and the X-ray powder diffraction data of the crystal form are shown in Table 7.

TABLE 7

| 2theta | d-spacing | Intensity % |
|---|---|---|
| 12.24 | 7.23 | 7.02 |
| 14.30 | 6.19 | 7.68 |
| 15.55 | 5.70 | 4.38 |
| 16.62 | 5.33 | 65.89 |
| 17.64 | 5.03 | 11.91 |
| 18.39 | 4.82 | 12.60 |
| 19.96 | 4.45 | 2.68 |
| 20.80 | 4.27 | 100.00 |
| 21.42 | 4.15 | 11.19 |
| 21.76 | 4.08 | 12.83 |
| 22.58 | 3.94 | 39.24 |
| 23.08 | 3.85 | 10.59 |
| 23.51 | 3.78 | 7.85 |
| 24.13 | 3.69 | 3.90 |
| 24.86 | 3.58 | 9.95 |
| 26.03 | 3.42 | 6.30 |
| 27.03 | 3.30 | 4.79 |
| 27.90 | 3.20 | 26.46 |
| 28.69 | 3.11 | 4.04 |
| 31.46 | 2.84 | 6.90 |

The data in Table 8 were obtained by using the same method as described in the example. A certain mass quantity of solids of crisaborole in free form were added to a certain volume of a positive solvent, and a certain volume of a reverse solvent was dropwise added thereto at room temperature while being magnetically stirred. The resultant mixture crystallized while being stirred, and then it was subjected to centrifugal separation and vacuum dried, to produce white solid crystals. The solids were determined by XRPD to be the crystal form

TABLE 8

| No. | Mass of starting material (mg) | Positive solvent | Volume of positive solvent (mL) | Reverse solvent | Volume of reverse solvent (mL) | Whether or not solids are precipitated | Resultant crystal form |
|---|---|---|---|---|---|---|---|
| 1 | 32.4 | acetone | 0.2 | water | 0.2 | Yes | Crystal form II |
| 2 | 29.6 | 1,4-dioxane | 0.2 | water | 0.2 | Yes | Crystal form II |
| 3 | 29.5 | tetrahydrofuran | 0.2 | water | 0.4 | Yes | Crystal form II |
| 4 | 28.8 | dimethylformamide | 0.2 | water | 0.4 | Yes | Crystal form II |
| 5 | 28.5 | Dimethyl sulfoxide | 0.2 | water | 0.4 | Yes | Crystal form II |

Example 6

200.5 mg of solids of crisaborole in free form were charged into a 20 mL glass bottle loaded with 5 mL of solvent acetone, and dissolved until the resultant mixture was clear. The opening of the bottle was sealed with a sealing membrane, and the membrane was pinked with a needle to form several small holes. The bottle was placed at room temperature to allow the solvent to slowly volatize, thereby to produce white solid crystals.

Figure 7:
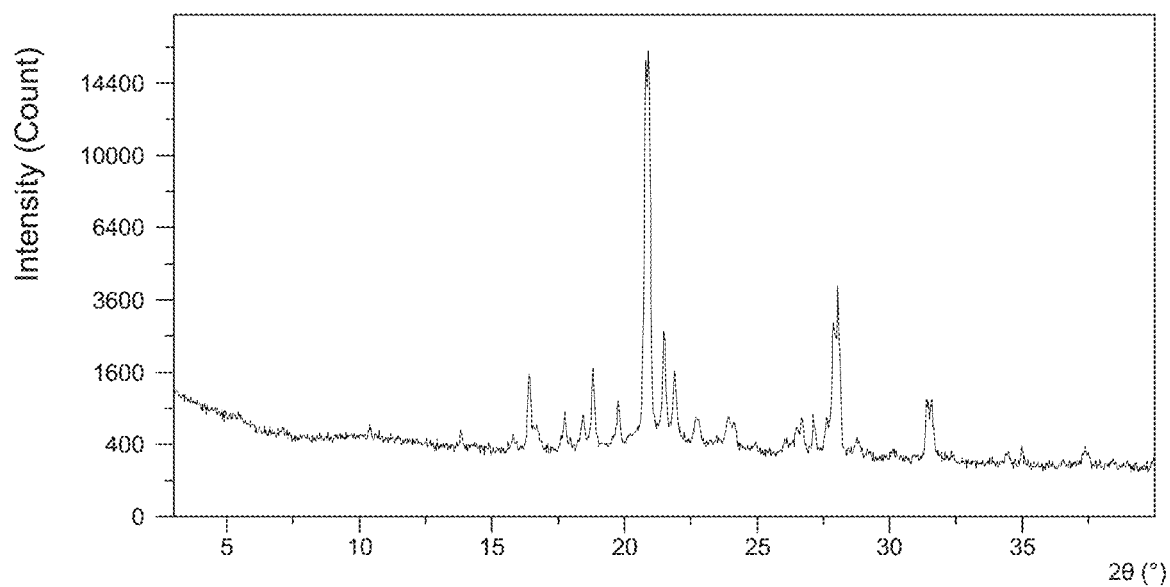
FIG. 7 is the X-ray powder diffraction pattern of the crystal form III as prepared in Example 6 of the invention.

It was found that the resultant solid crystals were the crystal form III as described in the invention by detection. The X-ray powder diffraction pattern of the crystal form is shown in FIG. 7, and the corresponding X-ray powder diffraction data are shown in Table 9.

Figure 8:
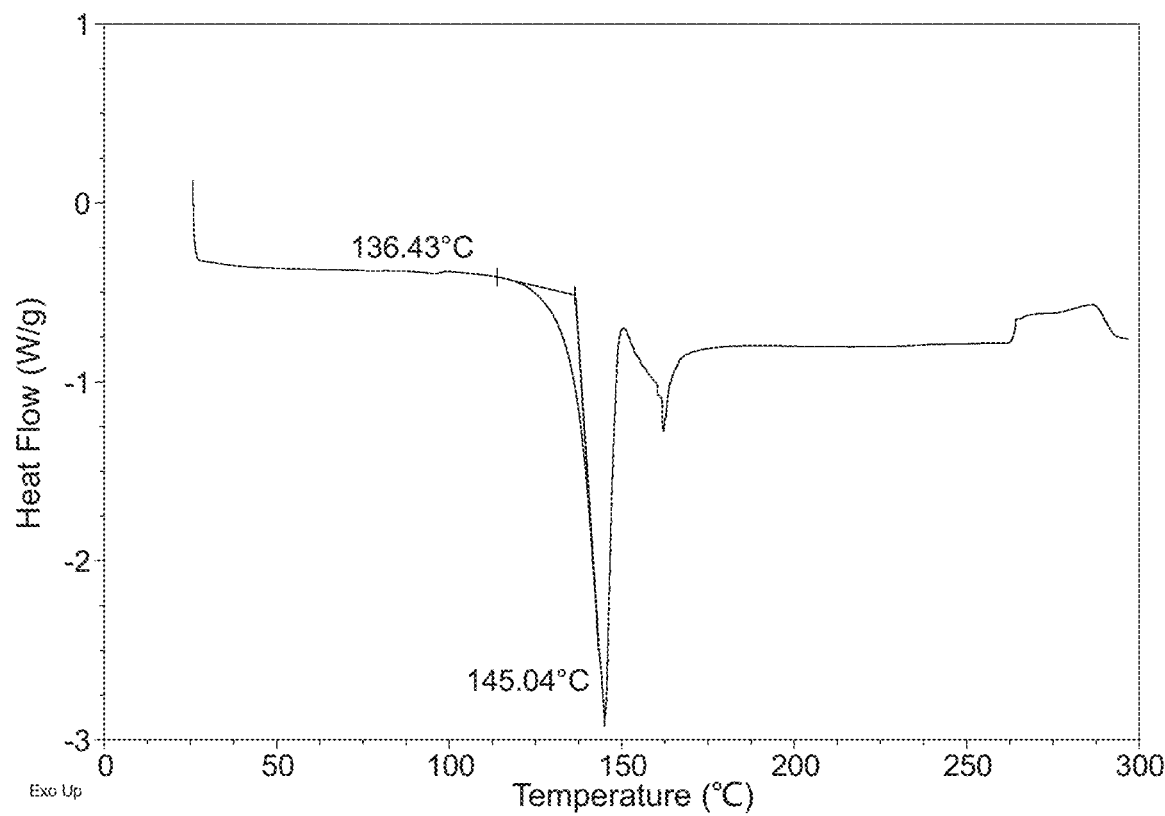
FIG. 8 is the DSC pattern of the crystal form III as prepared in Example 6 of the invention.
Figure 9:
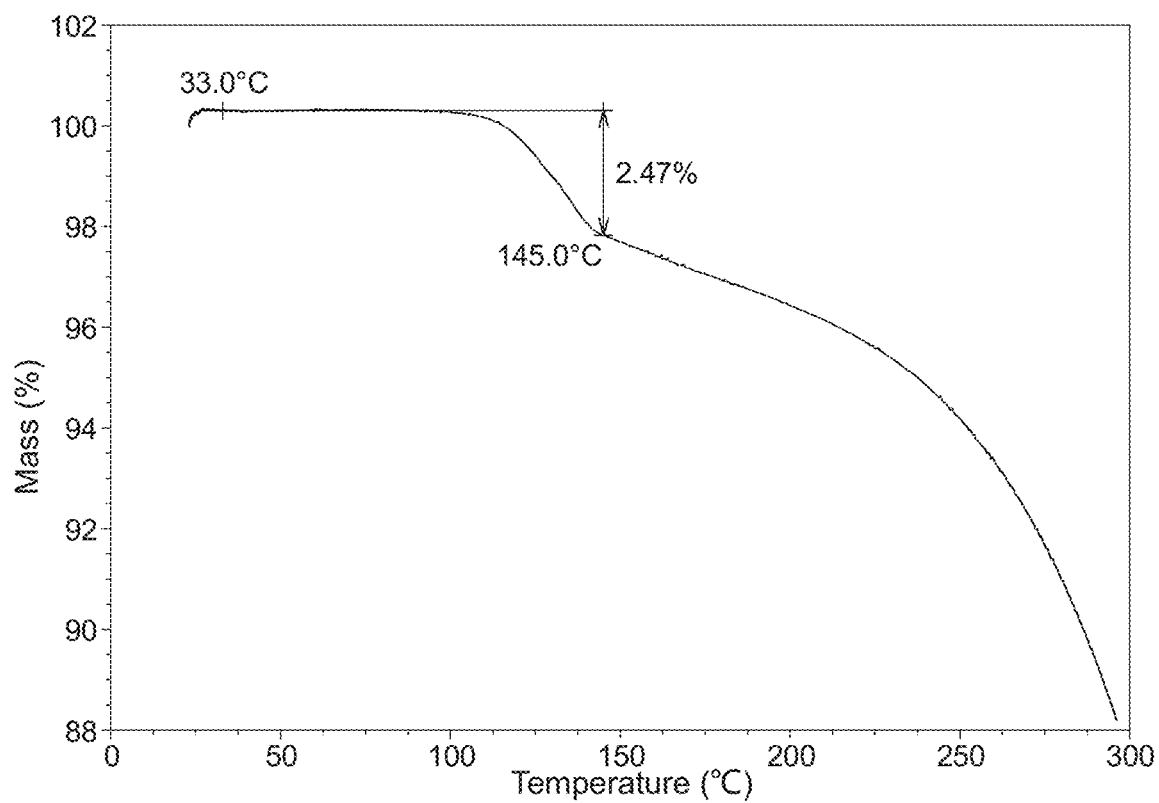
FIG. 9 is the TGA pattern of the crystal form III as prepared in Example 6 of the invention.

Upon conducting the differential scanning calorimetric analysis, the crystal form when being heated to a temperature in the vicinity of 136° C., involved heat absorption peaks, and its DSC is shown in FIG. 8. Upon conducting the thermogravimetric analysis, the crystal form III, when being heated to 145° C., had a mass lose gradient of about 2.5%, and its TGA is shown in FIG. 9. The crystal form III according to the invention is a hydrate.

TABLE 9

| 2theta | d-spacing | Intensity % |
|---|---|---|
| 10.20 | 8.67 | 1.03 |
| 13.63 | 6.49 | 1.19 |
| 16.21 | 5.47 | 7.54 |
| 17.55 | 5.05 | 3.06 |
| 18.24 | 4.86 | 2.64 |
| 18.62 | 4.77 | 8.91 |
| 19.58 | 4.53 | 3.64 |
| 20.59 | 4.31 | 100.00 |
| 20.72 | 4.29 | 91.97 |
| 21.30 | 4.17 | 12.98 |
| 21.69 | 4.10 | 7.34 |
| 22.49 | 3.95 | 2.14 |
| 23.70 | 3.75 | 2.18 |
| 23.95 | 3.72 | 1.80 |
| 26.29 | 3.39 | 2.04 |
| 26.50 | 3.36 | 2.82 |
| 26.93 | 3.31 | 2.79 |
| 27.41 | 3.25 | 2.88 |
| 27.86 | 3.20 | 22.34 |
| 31.38 | 2.85 | 5.26 |
| 37.17 | 2.42 | 1.12 |

Example 7

11.5 mg of solids of crisaborole in free form were added to 0.2 mL of acetone solvent, and the solvent volatilized at room temperature until it completely volatilized, to produce white solid crystals.

Figure 15:
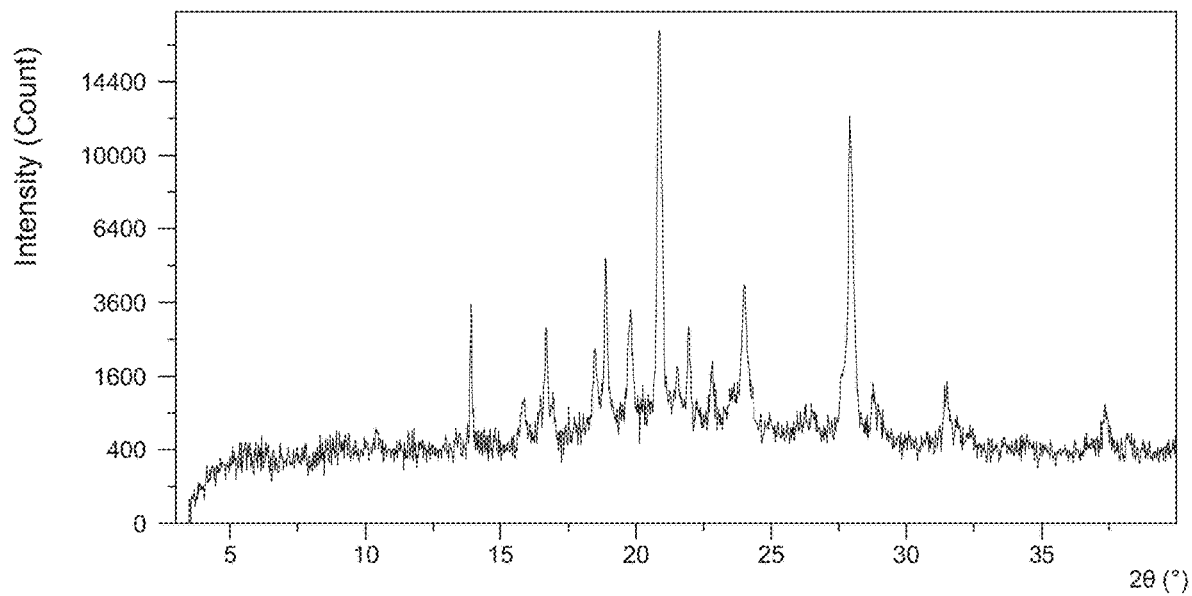
FIG. 15 is the X-ray powder diffraction pattern of the crystal form III as prepared in Example 7 of the invention.

It was found that the resultant solid crystals were the crystal form III as described in the invention by detection. The X-ray powder diffraction data of the crystal form are shown in FIG. 15 and Table 10.

TABLE 10

| 2theta | d-spacing | Intensity % |
|---|---|---|
| 13.66 | 6.48 | 16.96 |
| 15.63 | 5.67 | 3.67 |
| 16.43 | 5.40 | 13.85 |
| 18.22 | 4.87 | 8.94 |
| 18.62 | 4.76 | 27.66 |
| 19.54 | 4.54 | 14.45 |
| 20.58 | 4.32 | 100.00 |
| 21.26 | 4.18 | 5.22 |
| 21.70 | 4.10 | 10.34 |
| 22.54 | 3.94 | 6.87 |
| 23.74 | 3.75 | 19.42 |
| 26.01 | 3.43 | 2.08 |
| 27.67 | 3.22 | 67.83 |
| 28.51 | 3.13 | 3.66 |
| 31.19 | 2.87 | 3.78 |
| 37.12 | 2.42 | 3.30 |

Example 8

About 5 mg of crisaborole in free form were placed in a DSC(Q2000) tray, and the heating program was set as follows: the solids were heated to the temperature of 90° C., in a rate of 10° C./min; the solids were heated to the temperature of 130° C., in a rate of 5° C./min. The solids were balanced for 5 minutes, to produce white solid crystals.

Figure 10:
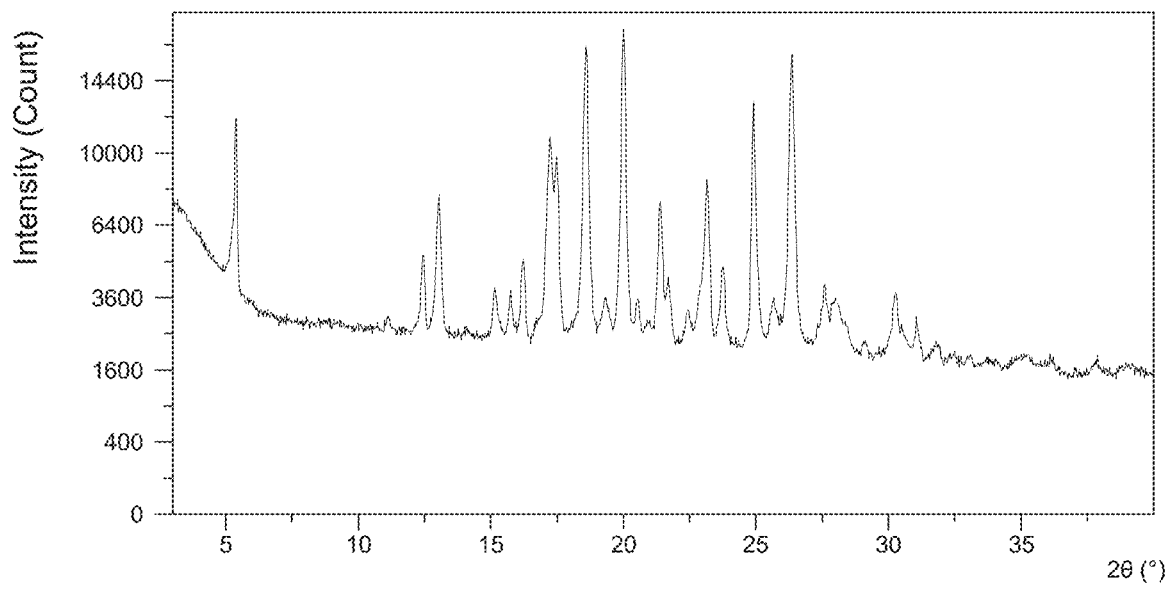
FIG. 10 is the X-ray powder diffraction pattern of the crystal form IV as prepared in Example 8 of the invention.

It was found that the resultant solid crystals were the crystal form IV as described in the invention by detection. The X-ray powder diffraction data of the crystal form are shown in FIG. 10 and Table 11.

TABLE 11

| 2theta | d-spacing | Intensity % |
|---|---|---|
| 5.34 | 16.54 | 44.99 |
| 12.42 | 7.13 | 16.46 |
| 13.01 | 6.80 | 34.31 |
| 15.12 | 5.86 | 9.66 |
| 15.72 | 5.64 | 9.34 |
| 16.20 | 5.47 | 16.87 |
| 17.19 | 5.16 | 52.62 |
| 17.47 | 5.08 | 44.48 |
| 18.56 | 4.78 | 92.02 |
| 19.29 | 4.60 | 6.44 |
| 19.98 | 4.44 | 100.00 |
| 20.50 | 4.33 | 6.81 |

TABLE 11-continued

| 2theta | d-spacing | Intensity % |
|---|---|---|
| 20.90 | 4.25 | 2.46 |
| 21.36 | 4.16 | 33.74 |
| 21.67 | 4.10 | 12.74 |
| 22.39 | 3.97 | 5.76 |
| 23.14 | 3.84 | 41.01 |
| 23.73 | 3.75 | 16.09 |
| 24.88 | 3.58 | 70.56 |
| 25.62 | 3.48 | 6.62 |
| 26.33 | 3.39 | 90.16 |
| 27.56 | 3.24 | 7.25 |
| 29.11 | 3.07 | 2.09 |
| 30.24 | 2.96 | 10.28 |
| 31.03 | 2.88 | 6.06 |
| 33.02 | 2.71 | 1.14 |
| 36.13 | 2.49 | 1.37 |

Example 9

About 11.5 mg of crisaborole in free form were weighted and charged into a glass bottle loaded with 0.2 mL of acetone solvent, and the resultant mixture volatilized at room temperature when exposed to air until the solvent completely volatilized. The precipitated solids were placed in a DSC (Q2000) tray, and the heating program was set as follows: the solids were heated to the temperature of 90° C., in a rate of 10° C./min; the solids were heated to the temperature of 145° C., in a rate of 5° C./min. The solids were balanced for 5 minutes, to produce white solid crystals.

Figure 16:
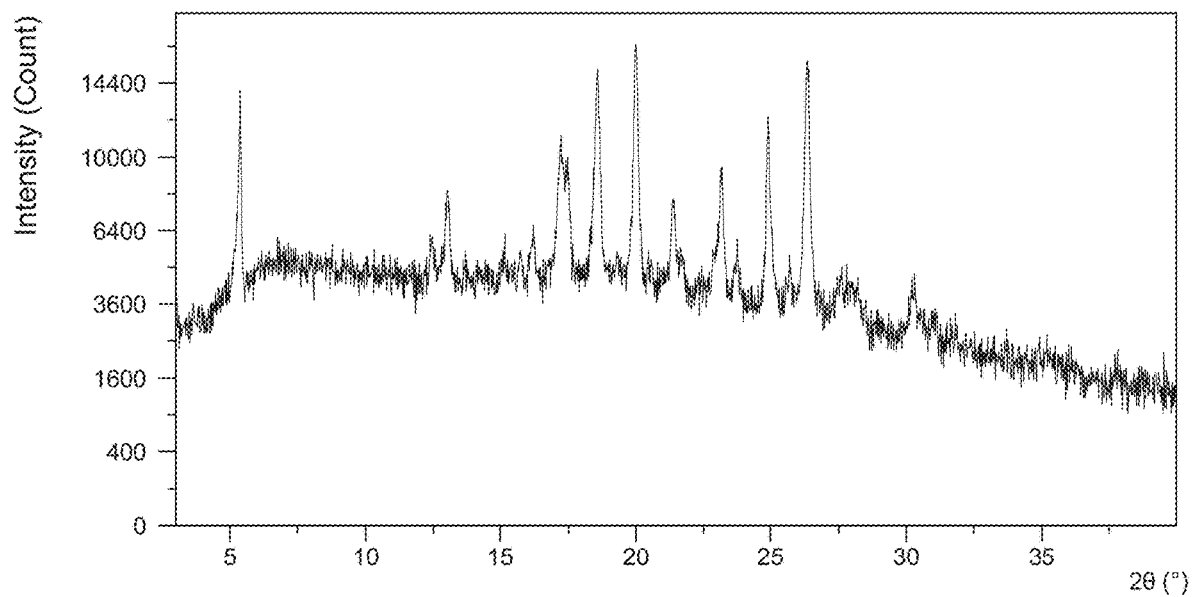
FIG. 16 is the X-ray powder diffraction pattern of the crystal form IV as prepared in Example 9 of the invention.
Figure 17:
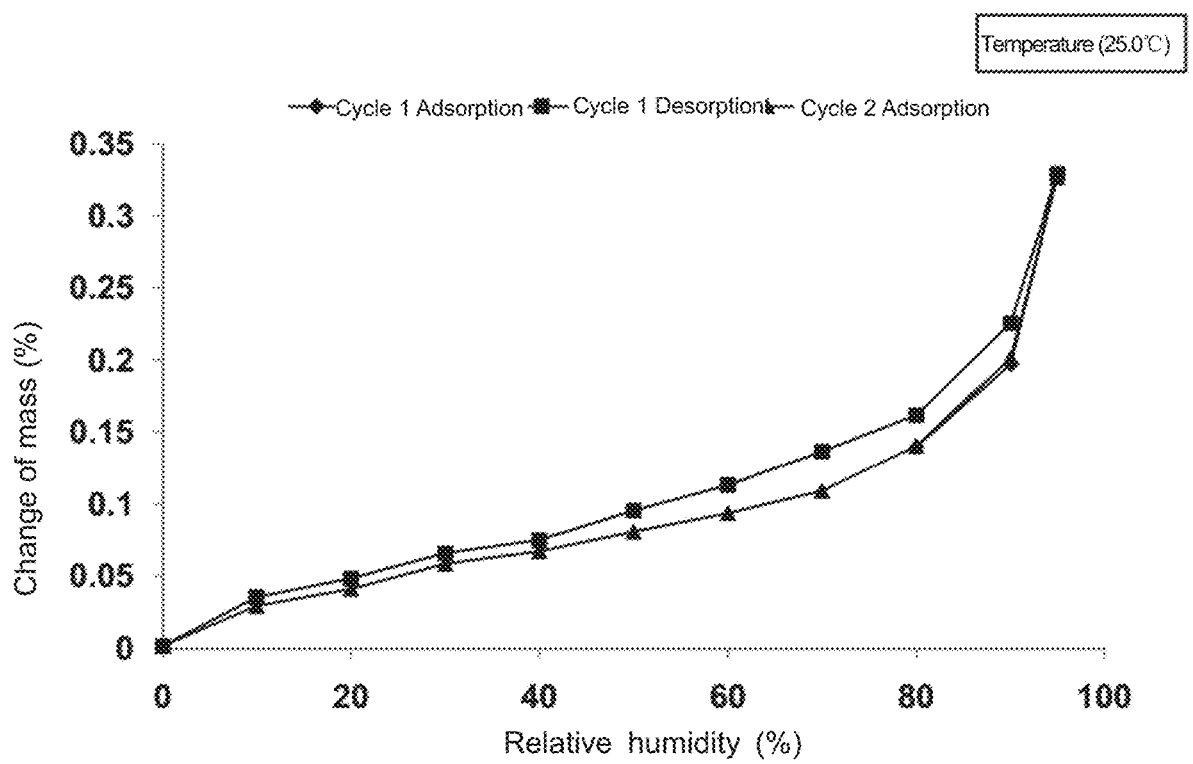
FIG. 17 is the DVS pattern of the crystal form I of the invention.
Figure 18:
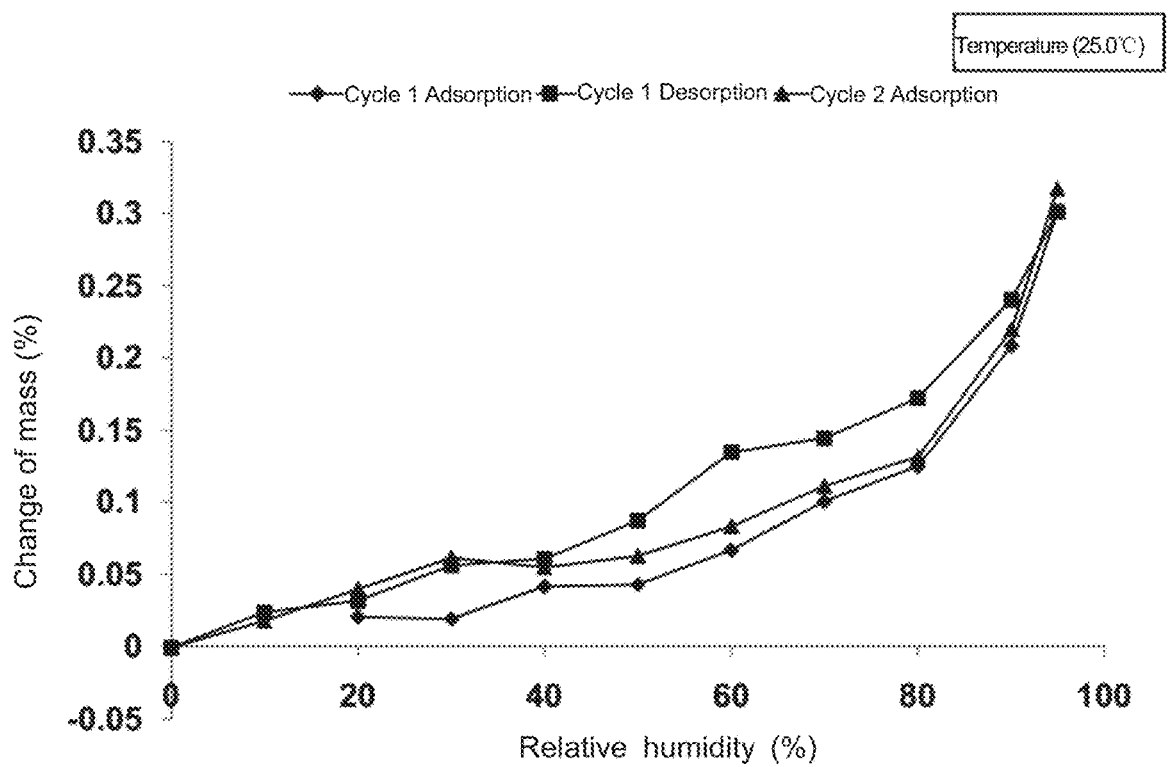
FIG. 18 is the DVS pattern of the crystal form II of the invention.
Figure 19:
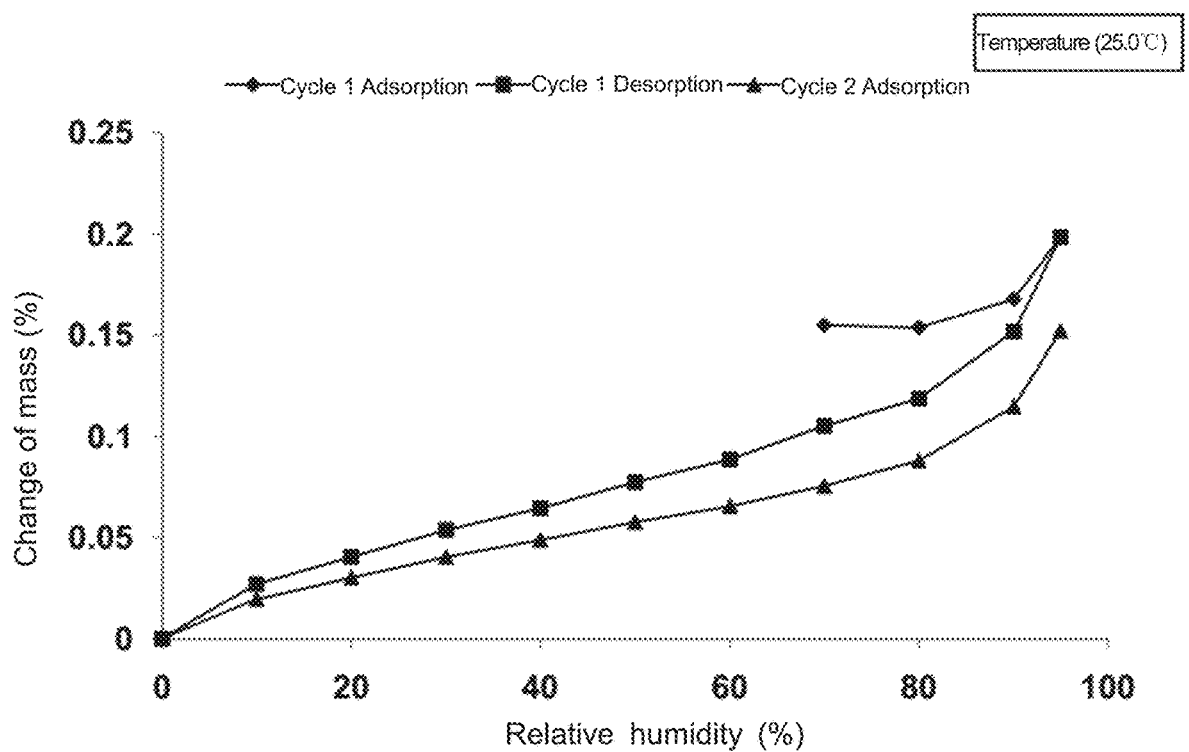
FIG. 19 is the DVS pattern of the crystal form III of the invention.
Figure 20:
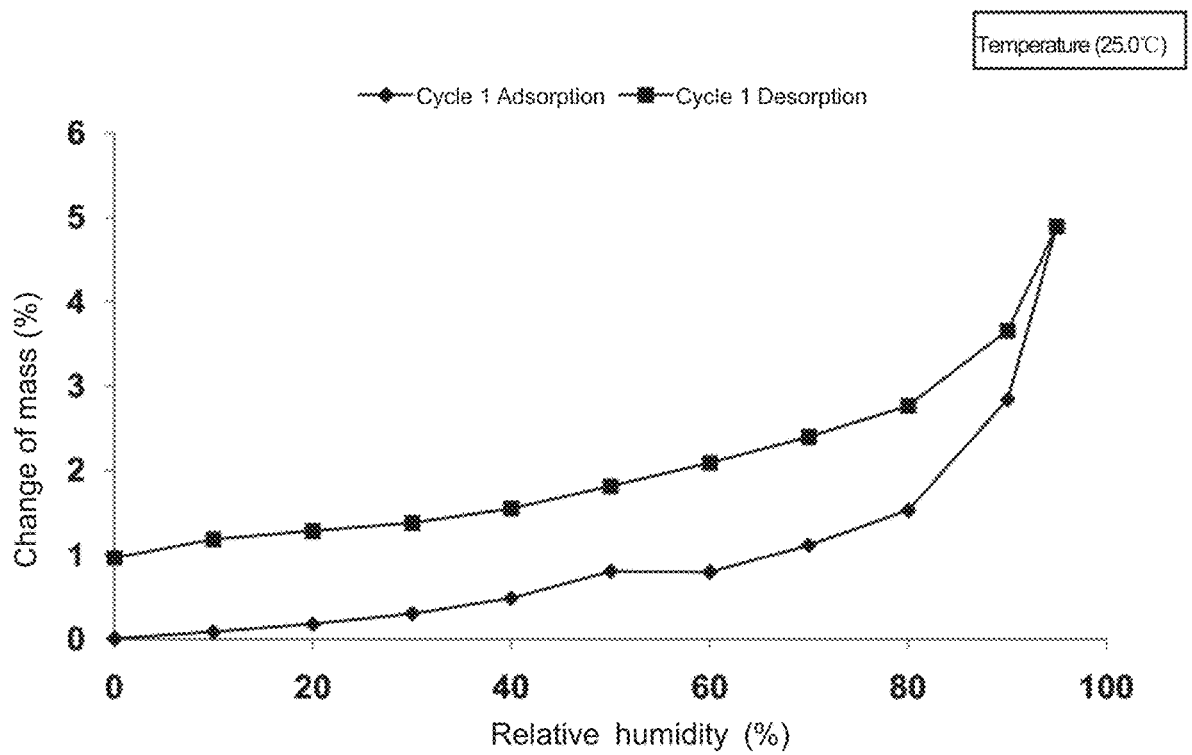
FIG. 20 is the DVS pattern of the crystal form IV of the invention.

It was found that the resultant solid crystals were the crystal form IV as described in the invention. The X-ray powder diffraction pattern of the crystal form is shown in FIG. 16 and the X-ray powder diffraction data of the crystal form are shown Table 12.

Figure 11:
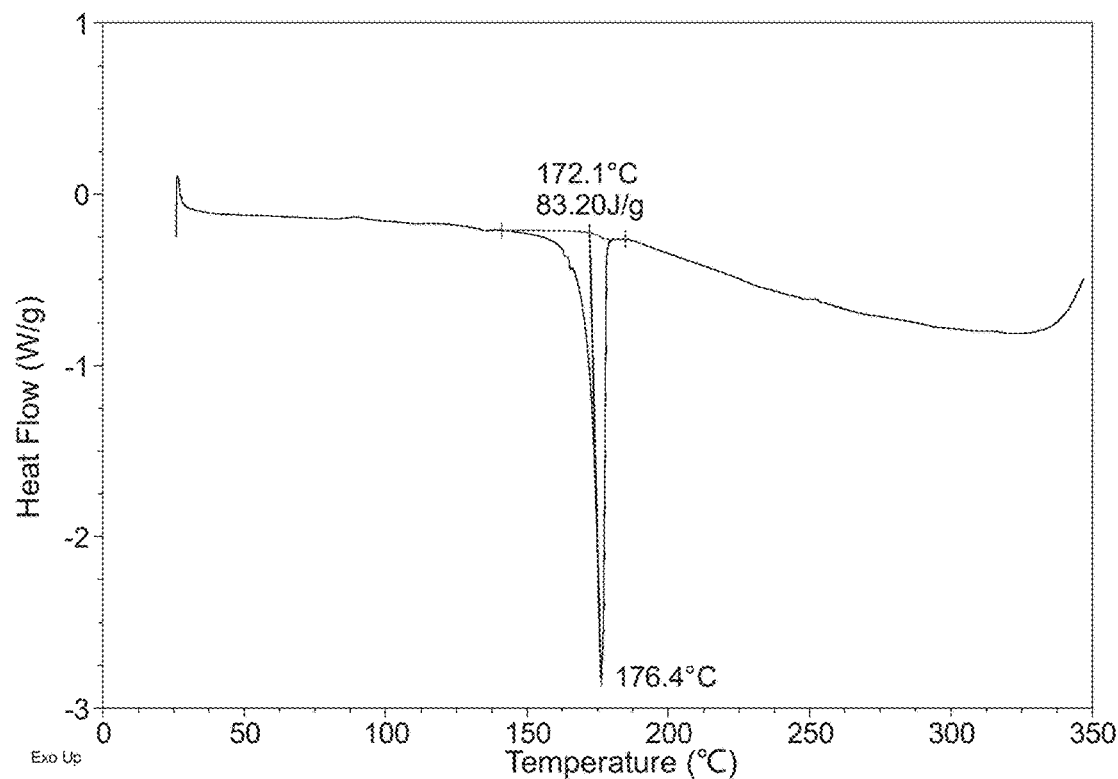
FIG. 11 is the DSC pattern of the crystal form IV as prepared in Example 9 of the invention.
Figure 12:
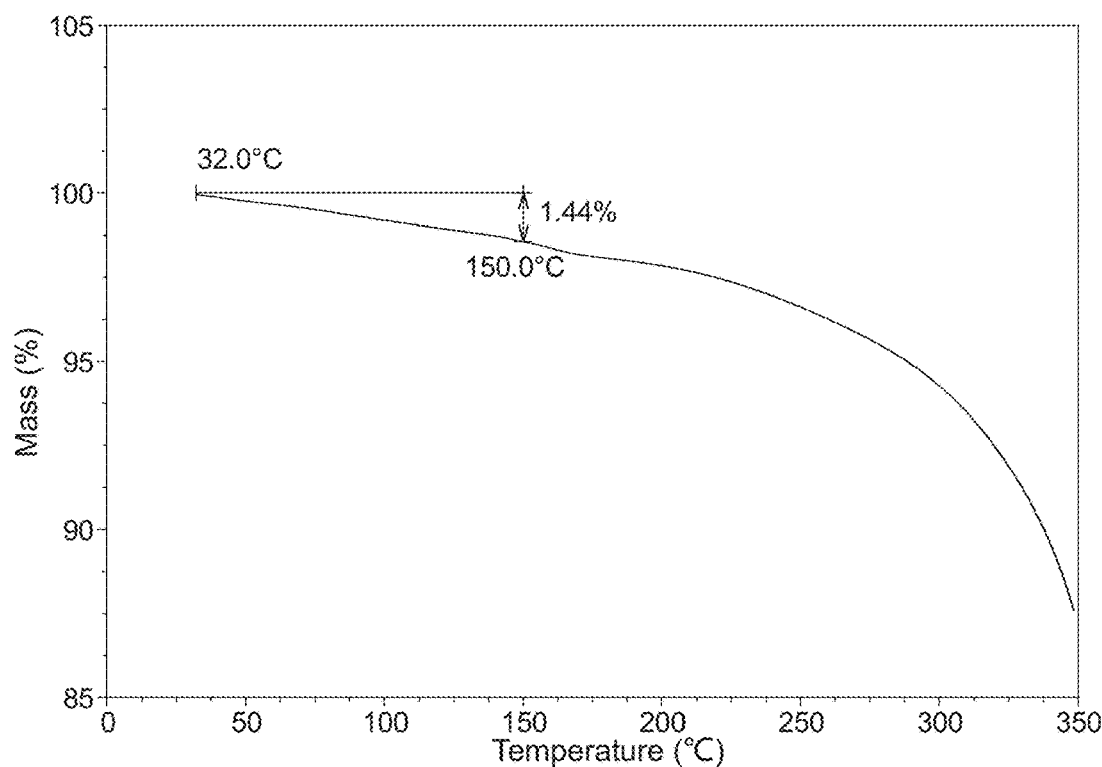
FIG. 12 is the TGA pattern of the crystal form IV as prepared in Example 9 of the invention.

Upon conducting the differential scanning calorimetric analysis, the crystal form IV, when being heated to a temperature in the vicinity of 172° C., involved heat absorption peaks, and its DSC is shown in FIG. 11. Upon conducting the thermogravimetric analysis, the crystal form IV, when being heated to 150° C., had a mass lose gradient of about 1.4%, and its TGA is shown in FIG. 12. The crystal form IV according to the invention is an anhydrate.

TABLE 12

| 2theta | d-spacing | Intensity % |
|---|---|---|
| 5.35 | 16.53 | 59.32 |
| 11.50 | 7.69 | 8.63 |
| 12.47 | 7.10 | 13.07 |
| 13.01 | 6.80 | 25.27 |
| 15.75 | 5.63 | 12.05 |
| 17.22 | 5.15 | 33.73 |
| 18.58 | 4.78 | 80.18 |
| 20.03 | 4.43 | 100.00 |
| 21.39 | 4.15 | 28.17 |
| 23.21 | 3.83 | 34.72 |
| 23.74 | 3.75 | 17.17 |
| 24.91 | 3.57 | 53.77 |
| 26.39 | 3.38 | 86.10 |
| 27.62 | 3.23 | 9.18 |

Test Part

Experimental Example 1 Study of Moisture Absorption

About 10 mg of the crystal form I, crystal form II, crystal form III and crystal form IV according to the invention were taken respectively to perform the dynamic vapor sorption (DVS) test. The obtained results were shown in Table 13:

TABLE 13

| Weight increase (%) | Relative humidity | |
|---|---|---|
| | Weight increase of 80% relative humidity | Weight increase of 95% relative humidity |
| Crystal form I | 0.14% | 0.32% |
| Crystal form II | 0.13% | 0.32% |
| Crystal form III | 0.09% | 0.15% |
| Crystal form IV | 1.53% | 4.90% |

The DVS patterns of the crystal form I, crystal form II, crystal form III and crystal form IV are respectively shown in FIG. 17, FIG. 18, FIG. 19 and FIG. 20.

With regard to the descriptions for the moisture absorption characteristic and the definition for the increased weight of moisture absorption (Guidelines for the Moisture Absorption Tests of Drugs in the Appendix of Chinese Pharmacopoeia (2015), Experimental conditions: 25° C.±1° C., 80% relative humidity):

Deliquescence: enough moisture is absorbed to form a liquid

High moisture absorption: the increased weight as caused by absorbing moisture is not less than 15.0%

Moisture absorption: the increased weight as caused by absorbing moisture is less than 15.0% but not less than 2.0%

Slight moisture absorption: the increased weight as caused by absorbing moisture is less than 2.0% but not less than 0.2%

No or almost no moisture absorption: the increased weight as caused by absorbing moisture is less than 0.2%.

The results show that according to the standards in Chinese Pharmacopoeia (2015), the crystal form I, crystal form II, and crystal form III of the invention almost have no moisture absorption, and the crystal IV has slight moisture absorption. Thus, each of the above crystal forms will not be ready to be influenced by high moisture so as to take the deliquescence. Particularly, even under the condition that the relative humidity was up to 95%, the crystal form I, crystal form II, and crystal form III of the invention still each have a low increased weight as caused by absorbing moisture, and thus they have more excellent deliquescence resistance.

Experimental Example 2 Study of Mechanical Stability

The crystal form I and crystal form IV of the invention were respectively placed in a mortar, and they were ground for 5 minutes by hand. The XRPD of the ground solids was tested, and the results were shown in Table 14:

TABLE 14

| Starting crystal form | Final crystal form |
|---|---|
| Crystal form I | Crystal form I |
| Crystal form IV | Crystal form IV |

Figure 21:
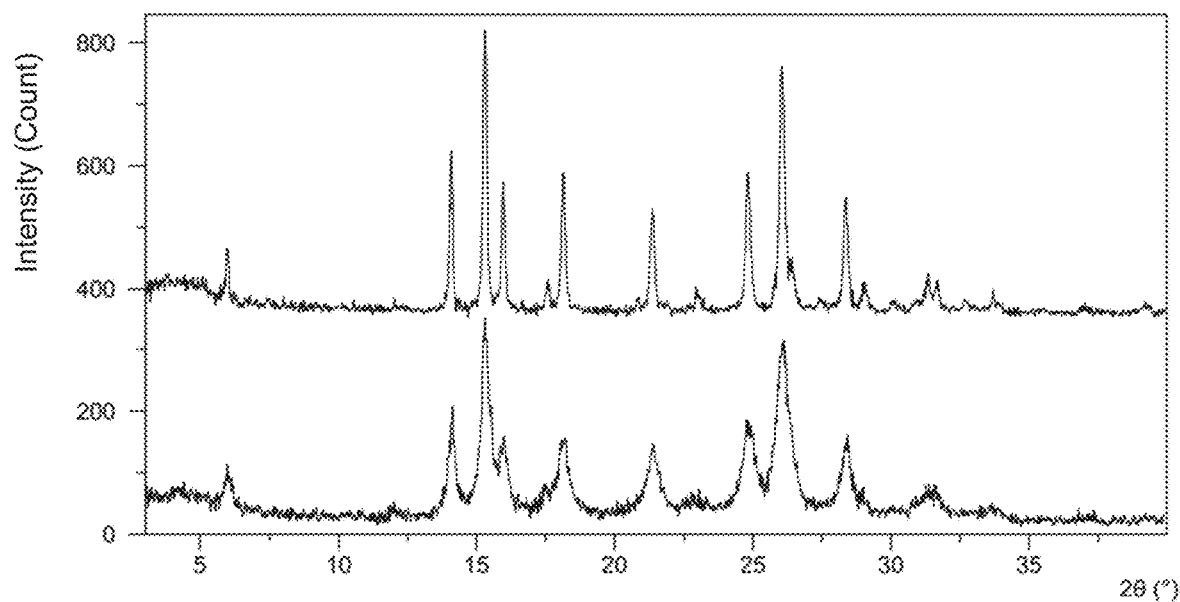
FIG. 21 is the diagram for showing the comparison in the XRPD patterns of the crystal form I according to the invention before and after grinding.
Figure 22:
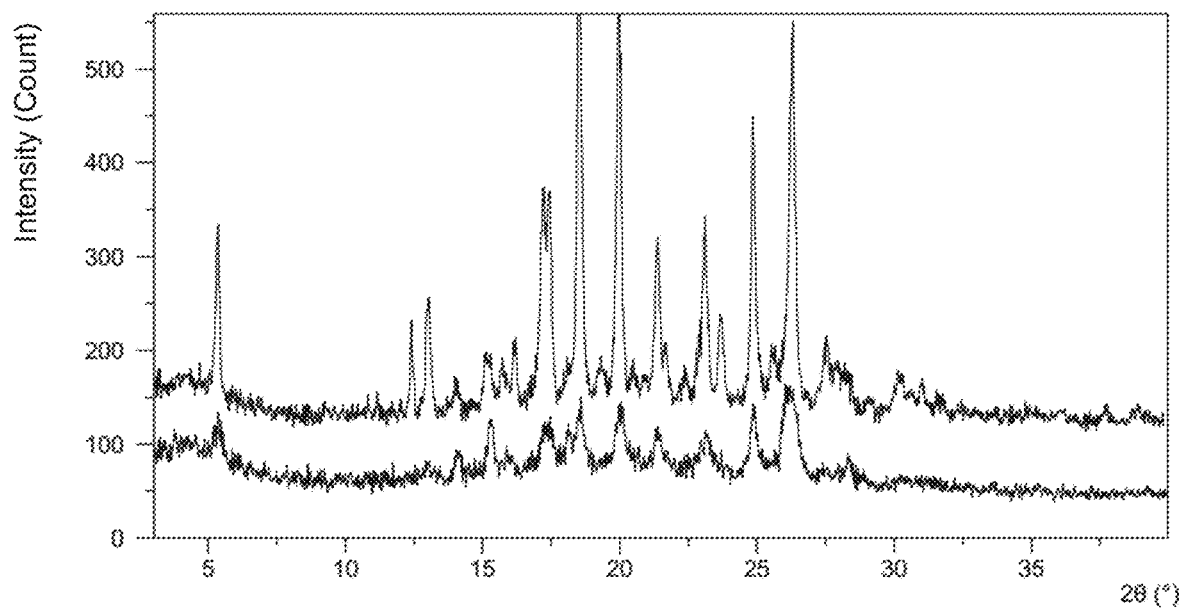
FIG. 22 is the diagram for showing the comparison in the XRPD patterns of the crystal form IV according to the invention before and after grinding.

The results show that under the action of certain mechanical stress, the crystal form I and crystal form IV of the invention are not changed, and they still can maintain stable physical and chemical properties. The diagrams for showing the comparison of the XRPD patterns before and after grinding of the crystal form I and the crystal form IV are respectively shown in FIG. 21 and FIG. 22 (the upper figure is the XRPD pattern before grinding, and the lower figure is the XRPD pattern after grinding for 5 minutes.

Experimental Example 3 Study of Dynamic Solubility

Samples of the crystal form I, crystal form II, crystal form III and crystal form IV of the invention were respectively formulated into a saturated solution with a fasting stimulated intestinal fluid (FaSSIF) with a pH of 6.5, a feeding state stimulated intestinal fluid (FeSSIF) with a pH of 5.0, a stimulated gastric fluid (SGF) with a pH of 1.8, and water, and the high performance liquid chromatography (HPLC) was used to respectively measure the amounts of compounds in the solutions at 1 h, 4 h and 24 h. The results are shown in Table 15.

figure, the upper pattern shows the XRPD pattern of the crystal forms before the storage, the middle pattern shows the XRPD pattern of the crystal forms after 3 months by being placed under the storage conditions of 25° C. and a 60% relative humidity, and the lower pattern shows the XRPD pattern of the crystal forms after 3 months by being placed under the conditions of 40° C. and a 75% relative humidity).

TABLE 15

|  |  | FaSSIF (pH = 6.5) | | | | FeSSIF (pH = 5.0) | | | |
| --- | --- | --- | --- | --- | --- | --- | --- | --- | --- |
|  | Time (h) | Crystal form I | Crystal form II | Crystal form III | Crystal form IV | Crystal form I | Crystal form II | Crystal form III | Crystal form IV |
| Solubility (mg/ml) | 1 | 0.006 | 0.011 | 0.008 | 0.009 | 0.044 | 0.018 | 0.025 | 0.062 |
|  | 4 | 0.007 | 0.005 | 0.010 | 0.017 | 0.059 | 0.049 | 0.067 | 0.061 |
|  | 24 | 0.012 | 0.008 | 0.012 | 0.013 | 0.059 | 0.055 | 0.074 | 0.056 |
|  |  | SGF (pH = 1.8) | | | | $H_2O$ | | | |
|  | Time (h) | Crystal form I | Crystal form II | Crystal form III | Crystal form IV | Crystal form I | Crystal form II | Crystal form III | Crystal form IV |
| Solubility (mg/ml) | 1 | 0.011 | 0.010 | 0.033 | 0.031 | 0.004 | 0.003 | 0.005 | ND |
|  | 4 | 0.037 | 0.026 | 0.034 | 0.027 | 0.005 | 0.001 | 0.004 | 0.006 |
|  | 24 | 0.038 | 0.015 | 0.040 | 0.026 | 0.006 | 0.006 | 0.006 | 0.004 |

ND: un-detected.

The crystal form I, crystal form II, crystal form III and crystal form IV of the invention each have a solubility that is in line with medicinal requirements.

Experimental Example 4 Study of Long-Term and Acceleration Stabilities

Samples of the crystal form I, crystal form II, and crystal form III of the invention were respectively placed under the conditions of 25° C. and a 60% relative humidity, and under the conditions of 40° C. and a 75% relative humidity, and the results of the changes in the crystal form are shown in Table 16:

TABLE 16

| Starting crystal form | Storage condition | Storage time | Changes of crystal form |
| --- | --- | --- | --- |
| Crystal form I | 25° C., 60% relative humidity | 3 months | Crystal form I remained unchanged |
| Crystal form I | 40° C., 75% relative humidity | 3 months | Crystal form I remained unchanged |
| Crystal form II | 25° C., 60% relative humidity | 3 months | Crystal form II remained unchanged |
| Crystal form II | 40° C., 75% relative humidity | 3 months | Crystal form II remained unchanged |
| Crystal form III | 25° C., 60% relative humidity | 3 months | Crystal form III remained unchanged |
| Crystal form III | 40° C., 75% relative humidity | 3 months | Crystal form III remained unchanged |

Figure 23:
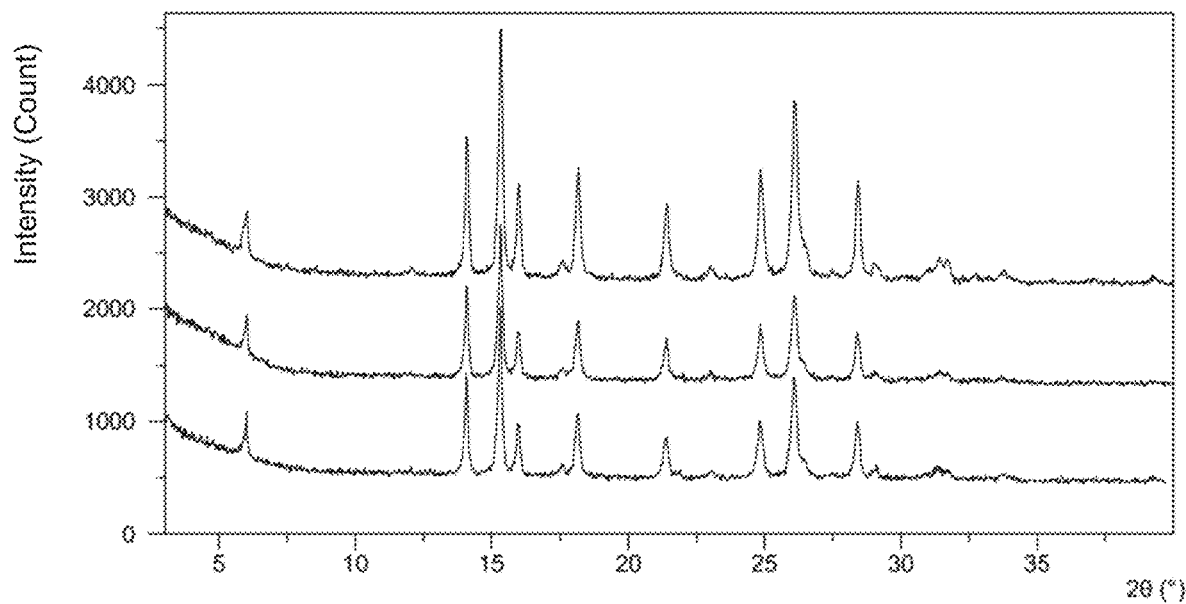
FIG. 23 is the diagram for showing the comparison in the XPRD pattern between the longer-term stability and acceleration stability of the crystal form I according to the invention.
Figure 24:
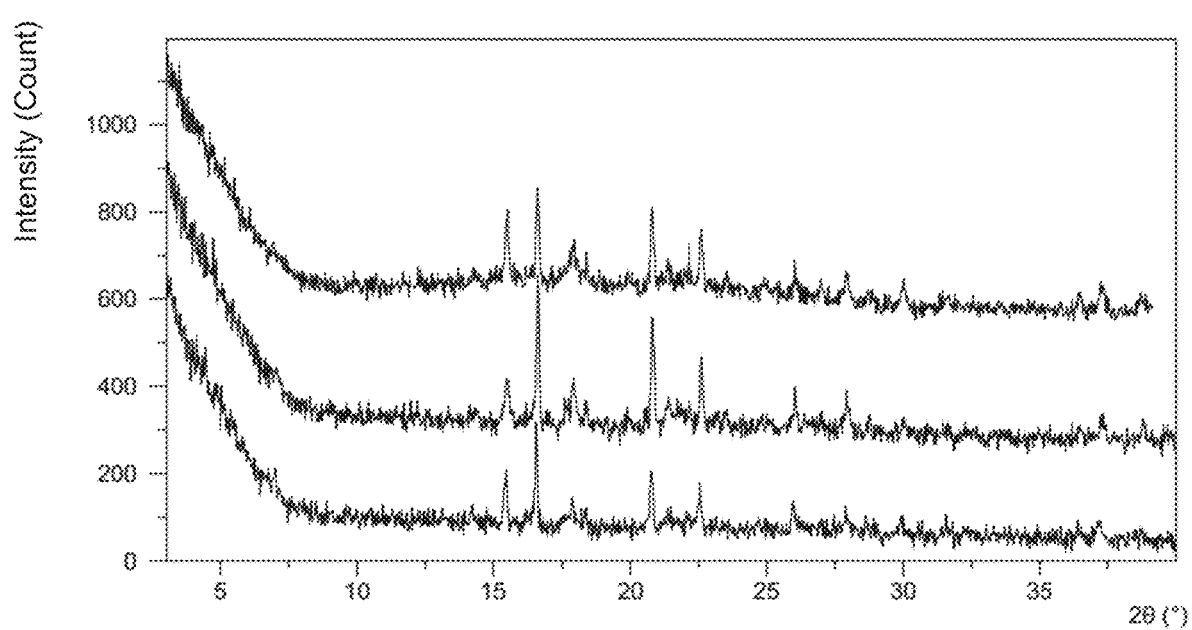
FIG. 24 is the diagram for showing the comparison in the XPRD pattern between the longer-term stability and acceleration stability of the crystal form II according to the invention.
Figure 25:
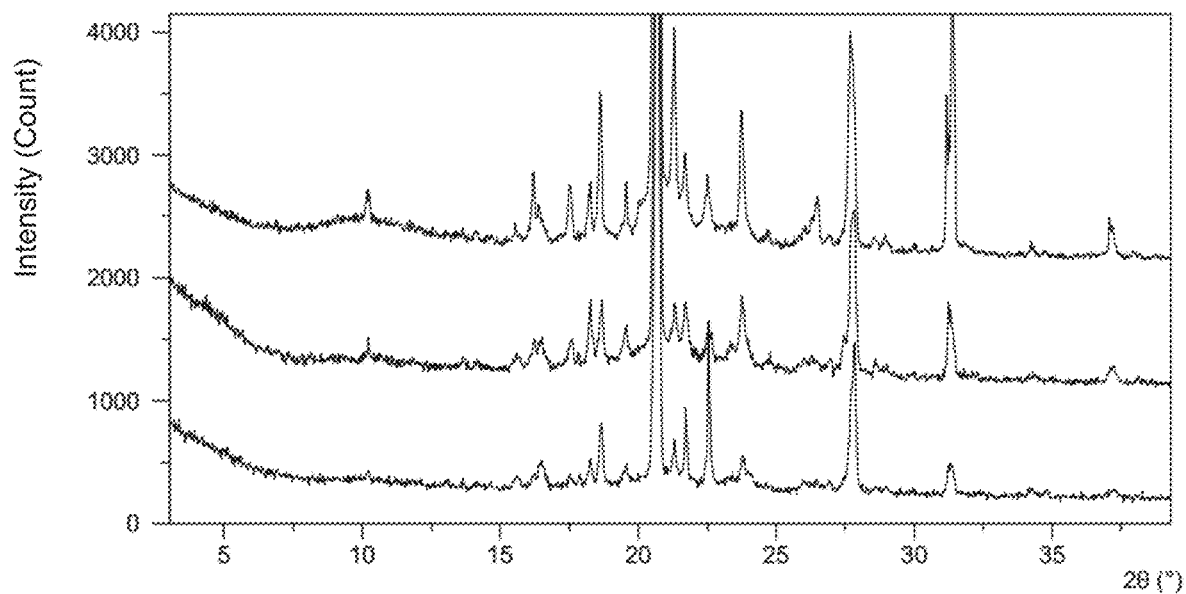
FIG. 25 is the diagram for showing the comparison in the XPRD pattern between the longer-term stability and acceleration stability of the crystal form III according to the invention.

The results show that the crystal form I, crystal form II and crystal form Ill of the invention can still maintain their stability placed in the two kinds of humidity for 3 months. The XRPD diagrams for showing the comparisons in the long-term and acceleration stabilities of the crystal form I, crystal form II, and crystal form Ill of the invention are respectively shown in FIG. 23, FIG. 24 and FIG. 25 (in each Experimental Example 5 Study of Particle Size Distribution Particle Size Comparative Test:
Samples of the crystal form I, crystal form II, crystal form III, and crystal form IV of the invention were taken to carry out the particle size distribution test.
The results of the particle size distribution are shown in Table 17:

TABLE 17

| Crystal form | MV (μm) | D10 (μm) | D50 (μm) | D90 (μm) |
| --- | --- | --- | --- | --- |
| Crystal form I | 9.62 | 1.69 | 5.52 | 20.35 |
| Crystal form II | 23.13 | 8.24 | 20.46 | 40.42 |
| Crystal form III | 289.0 | 21.68 | 163.0 | 903.1 |
| Crystal form IV | 52.95 | 13.43 | 33.68 | 99.36 |

Note:
MV represents average particle size as calculated in terms of the volume
D10 represents the particle size corresponding to 10% of the particle size distribution (volume distribution)
D50 represents the particle size corresponding to 50% of the particle size distribution (volume distribution), also called as median size
D90 represents the particle size corresponding to 90% of the particle size distribution (volume distribution).

Note:
MV represents average particle size as calculated in terms of the volume
D10 represents the particle size corresponding to 10% of the particle size distribution (volume distribution)
D50 represents the particle size corresponding to 50% of the particle size distribution (volume distribution), also called as median size
D90 represents the particle size corresponding to 90% of the particle size distribution (volume distribution).

Figure 26:
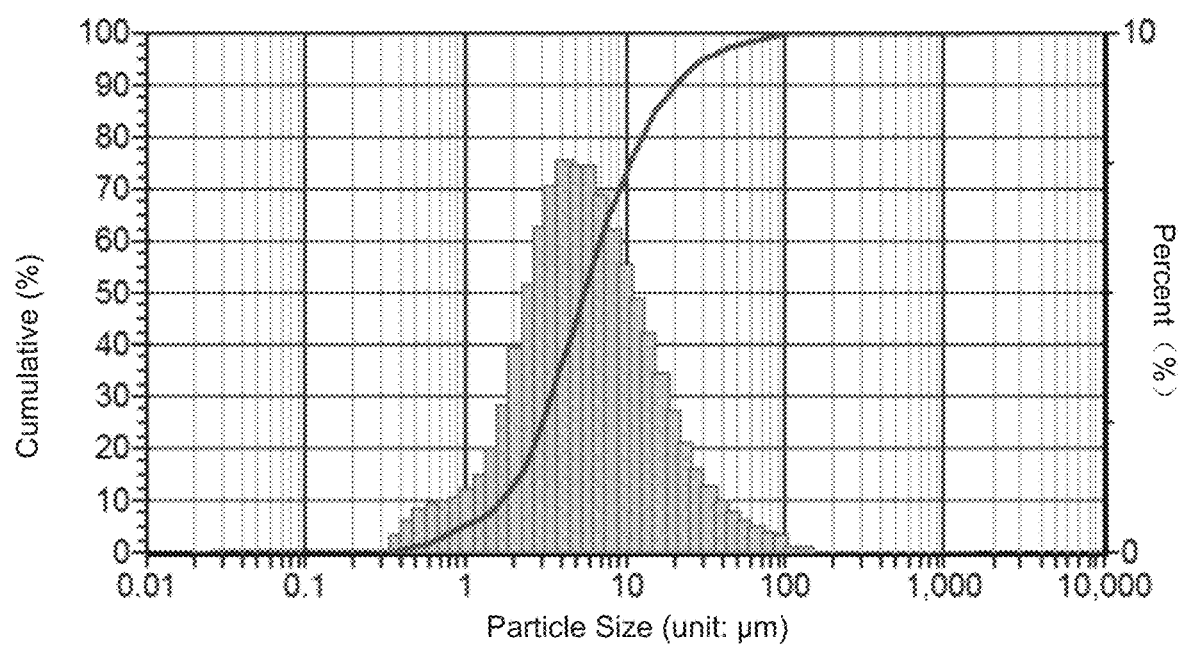
FIG. 26 is the PSD pattern of the crystal form I of the invention.
Figure 27:
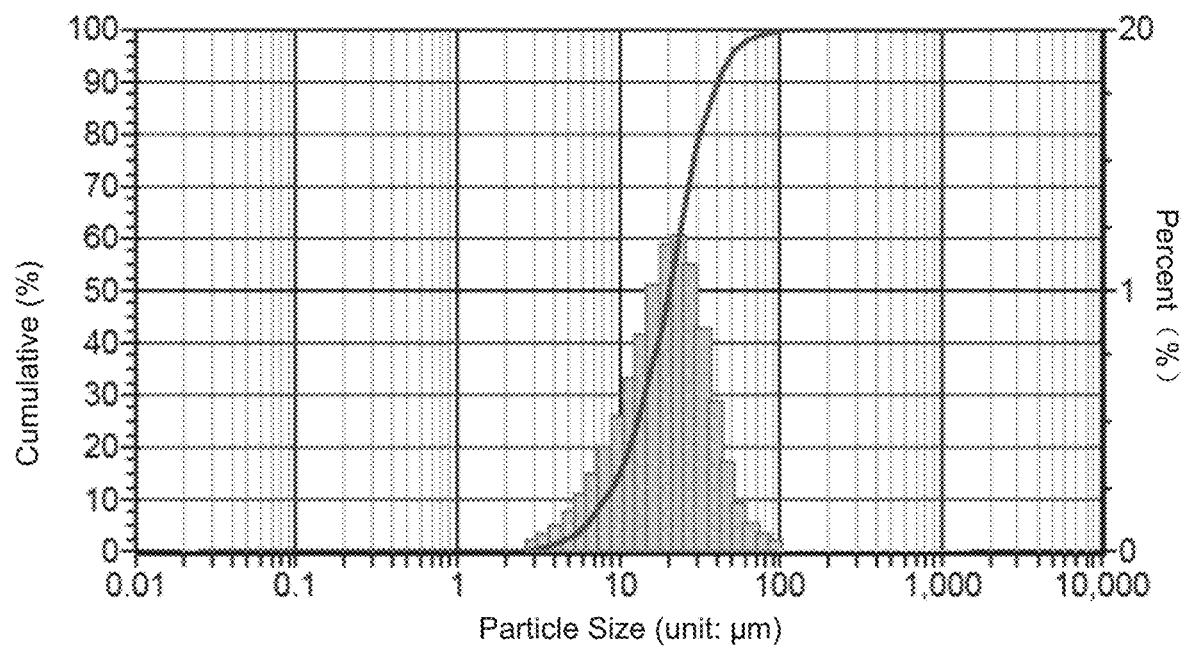
FIG. 27 is the PSD pattern of the crystal form II of the invention.
Figure 28:
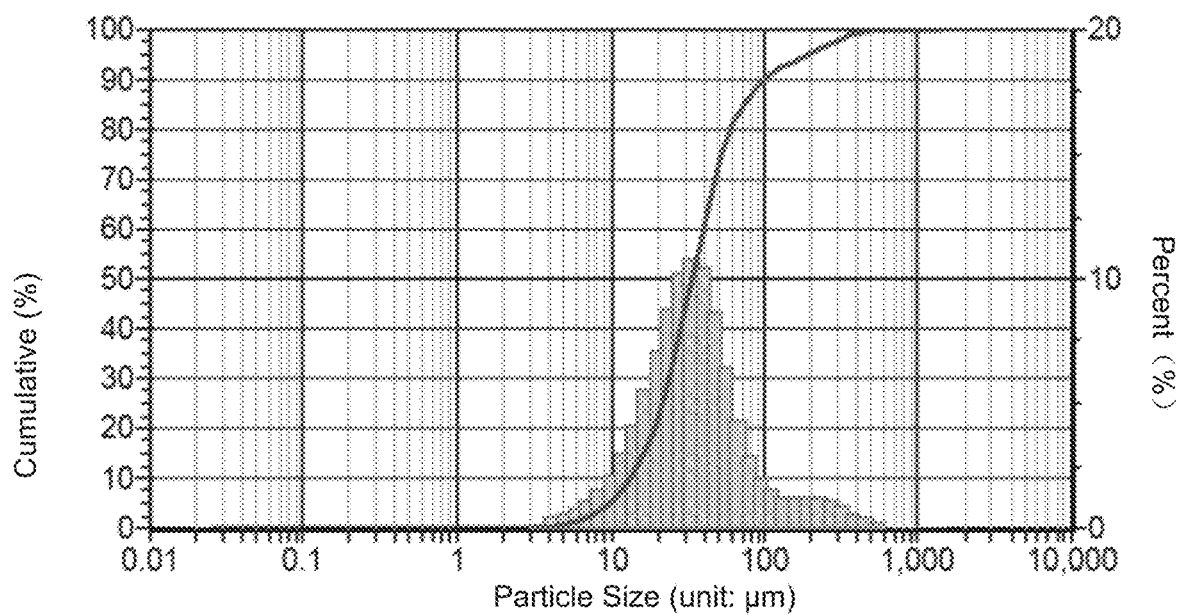
FIG. 28 is the PSD pattern of the crystal form IV of the invention.

The PSD patterns of the crystal form I, the crystal form II and the crystal form IV are respectively shown in FIG. 26, FIG. 27 and FIG. 28, and from these figures, it can be seen that the particle size distributions of the crystal form I, the crystal form II and the crystal form IV are homogeneous.

Figure 29:
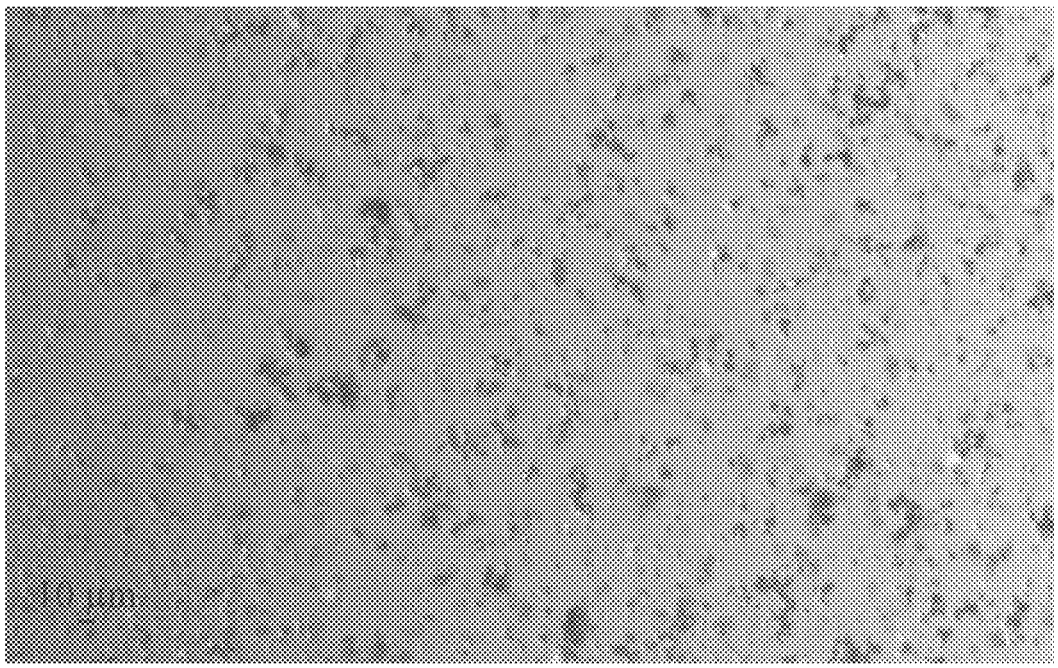
FIG. 29 is the PLM pattern of the crystal form I of the invention.
Figure 30:
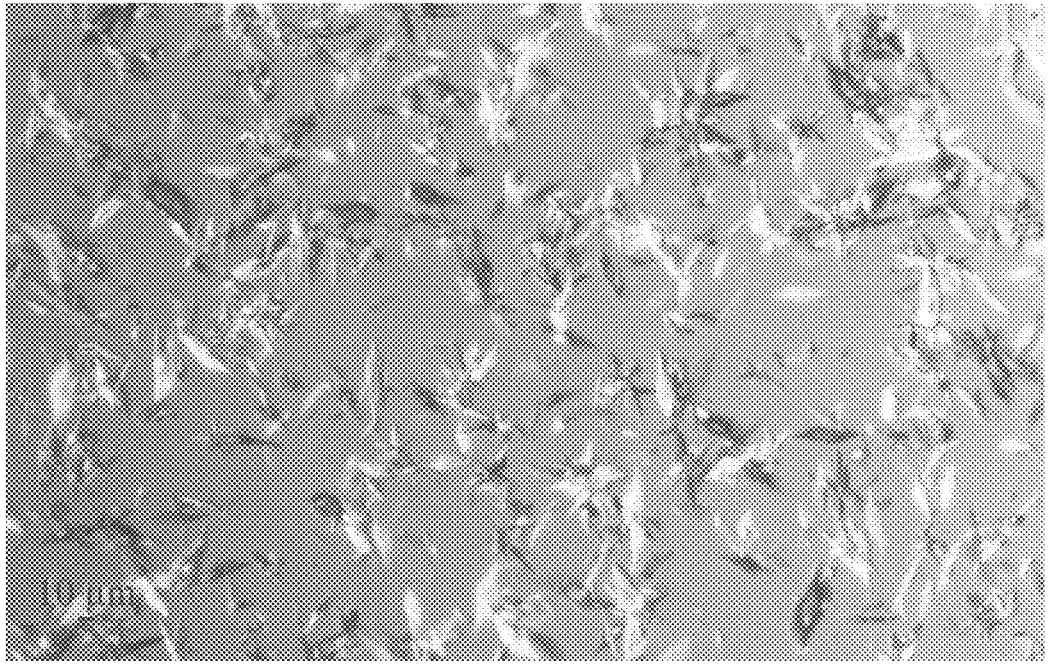
FIG. 30 is the PLM pattern of the crystal form II of the invention.
Figure 31:
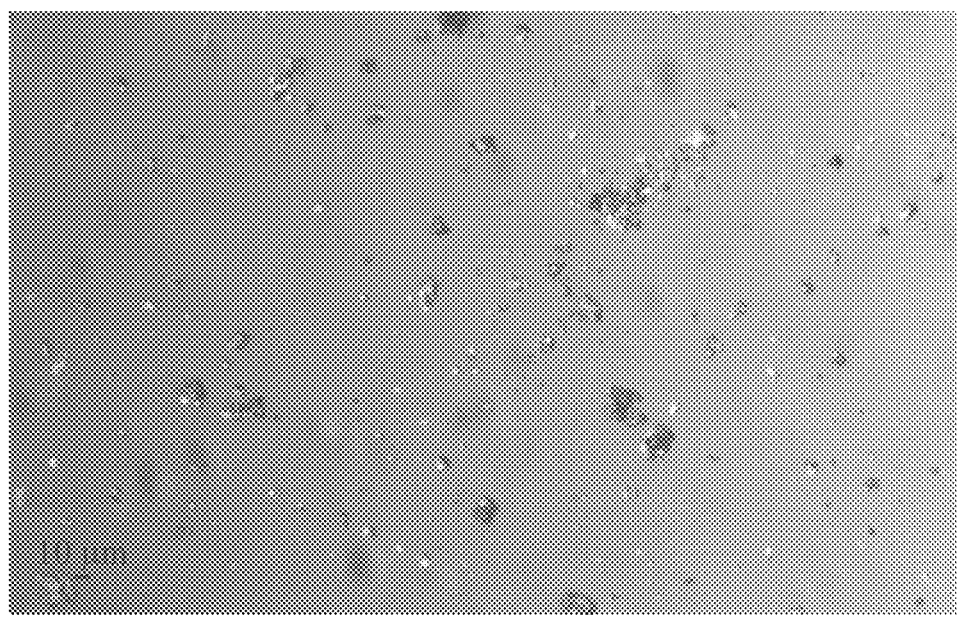
FIG. 31 is the PLM pattern of the crystal form IV of the invention.

In addition, the PLM patterns of the crystal form I, the crystal form II and the crystal form IV are respectively shown in FIG. 29, FIG. 30 and FIG. 31, and from these figures, it can be seen that the particle sizes of the particles of the crystal form I, the crystal form II and the crystal form IV are homogeneous.

The homogenous particle size can help to simplify the post-treatment processes of the formulation, and to increase quantity controls.

A person skilled in the art could understand that under the teachings of the description, some variations or changes to the invention are allowable. These variations and changes also should be in the scope as defined by the claims in the invention.

The invention claimed is:

1. A method of preparing crisaborole crystal form I comprising the steps of dissolving crisaborole in a single volatile solvent and allowing the single volatile solvent to volatilize to provide the crisaborole crystal form I, wherein the single volatile solvent is selected from the group consisting of alkyl nitriles, alkyl ethers, halogenated hydrocarbons and esters.

2. The method according to claim 1 wherein the single volatile solvent is selected from the group consisting of acetonitrile, methyl tert-butyl ether, chloroform, dichloromethane, and ethyl acetate.

3. A method of preparing crisaborole crystal form II comprising the steps of suspending crisaborole in a mixed solvent of water and an alcohol, stirring the suspension, subjecting the suspension to centrifugal separation and drying the suspension to provide crisaborole crystal form II, wherein the water to alcohol volume ratio is 1:1.

4. A method of preparing crisaborole crystal form III comprising the steps of dissolving crisaborole in a ketone solvent until the resultant mixture is clear, and the resultant mixture is subjected to volatile crystallization, to provide crisaborole crystal form III.

5. The method according to claim 4 wherein the ketone solvent is acetone.

6. A method of preparing crisaborole crystal form I comprising the steps of suspending crisaborole in a single solvent to give a suspension wherein the suspension is stirred, subjected to separation, and dried, to provide the crystal form I of crisaborole, wherein the single solvent is selected from the group consisting of water and toluene.

7. A method of preparing crisaborole crystal form I comprising the steps of suspending crisaborole in a mixed solvent to give a suspension wherein the suspension is stirred, subjected to separation, and dried, to provide the crisaborole crystal form I, wherein the mixed solvent is water and a further solvent wherein the further solvent is selected from the group consisting of alcohols, alkyl nitriles, esters, ketones, amides, cyclic ethers and dimethyl sulfoxide, wherein the volume of the water is greater than the volume of the further solvent.

8. The method of claim 7 wherein the further solvent is selected from the group consisting of isopropanol, acetonitrile, isopropyl acetate, acetone, dimethyl formamide, 1,4-dioxane, and dimethyl sulfoxide.

9. A method of preparing crisaborole crystal form I comprising the steps of suspending crisaborole in a mixed solvent to give a suspension wherein the suspension is stirred, subjected to separation, and dried, to provide the crystal form I of crisaborole, wherein the mixed solvent is a hydrocarbon and a further solvent selected from the group consisting of ketones, esters, cyclic ethers, halogenated hydrocarbons and alcohols.

10. The method of claim 9 wherein the hydrocarbon is n-heptane and the further solvent is selected from the group consisting of methyl isobutyl ketone, ethyl acetate, 2-methyltetrahydrofuran, chloroform, and ethanol, wherein the volume of the n-heptane is less than the volume of the further solvent.

11. A method of preparing crisaborole crystal form I comprising the steps of suspending crisaborole in a mixed solvent to give a suspension wherein the suspension is stirred, subjected to separation, and dried, to provide the crystal form I of crisaborole, wherein the mixed solvent is toluene and a halogenated hydrocarbon.

12. The method of claim 11 wherein the halogenated hydrocarbon is dichloromethane and wherein the volume of the dichloromethane is less than the volume of the toluene.

13. A method of preparing crisaborole crystal form II comprising the steps of dissolving crisaborole in a positive solvent, adding a reverse solvent, stirring until crystallization, separation via centrifugal separation, and drying to provide crisaborole crystal form II, wherein the positive solvent is selected from the group consisting of alcohols, ketones, cyclic ethers, amides, and dimethyl sulfoxide, and the reverse solvent is water, wherein the volume of the water is equal to or greater than the volume of the positive solvent.

14. The method according to claim 13 wherein the positive solvent is selected from the group consisting of isopropanol, acetone, 1,4-dioxane, tetrahydrofuran, dimethylformamide, and dimethylsulfoxide.

* * * * *